US006080570A

United States Patent [19]
Chladek et al.

[11] Patent Number: 6,080,570
[45] Date of Patent: *Jun. 27, 2000

[54] METHOD OF PRODUCING A VACCINE FOR SWINE INFERTILITY AND RESPIRATORY SYNDROME

[75] Inventors: Danny W. Chladek; Louis L. Harris; David E. Gorcyca, all of St. Joseph, Mo.

[73] Assignee: Boehringer Ingelheim Vetmedica, Inc., St. Joseph, Mo.

[*] Notice: This patent is subject to a terminal disclaimer.

[21] Appl. No.: 08/927,052

[22] Filed: Sep. 10, 1997

Related U.S. Application Data

[60] Continuation of application No. 08/316,529, Sep. 30, 1994, Pat. No. 5,846,805, which is a division of application No. 08/301,738, Sep. 6, 1994, abandoned, which is a continuation of application No. 07/860,444, Mar. 30, 1992, abandoned, which is a continuation-in-part of application No. 07/749,839, Aug. 26, 1991, abandoned, which is a continuation-in-part of application No. 07/760,713, Sep. 16, 1991, abandoned.

[51] Int. Cl.[7] .............................. C12N 7/00; C12N 7/04; C12N 7/08; C12N 7/02

[52] U.S. Cl. ...................... 435/235.1; 435/236; 435/237; 435/239; 424/815

[58] Field of Search ................................. 435/235.1, 236, 435/237, 239; 424/815

[56] References Cited

U.S. PATENT DOCUMENTS

| | | | |
|---|---|---|---|
| 4,753,884 | 6/1988 | Kit et al. | 424/205.1 |
| 4,810,493 | 3/1989 | Patrick et al. | . |
| 5,476,778 | 12/1995 | Chladek et al. | 435/235.1 |
| 5,510,258 | 4/1996 | Sanderson et al. | 435/237 |
| 5,587,164 | 12/1996 | Sanderson et al. | 424/218.1 |
| 5,597,721 | 1/1997 | Brun et al. | 435/235.1 |
| 5,677,429 | 10/1997 | Benfiled | 530/388.3 |
| 5,683,865 | 11/1997 | Collins et al. | 435/5 |
| 5,840,563 | 11/1998 | Chladek et al. | 435/235.1 |
| 5,846,805 | 12/1998 | Collins et al. | 435/235.1 |

FOREIGN PATENT DOCUMENTS

| | | |
|---|---|---|
| 208672 | of 0000 | European Pat. Off. . |
| 2602791 | of 0000 | France . |
| 62-198626 | of 0000 | Japan . |
| WO 89/08701 | of 0000 | WIPO . |
| WO 88/03410 | 5/1988 | WIPO . |
| WO 92/21375 | 6/1992 | WIPO . |
| WO 92/21375 | 12/1992 | WIPO . |
| WO 96/36356 | 11/1996 | WIPO . |

OTHER PUBLICATIONS

Carrascosa et al., *Journal of Virological Methods*, 3 303–310, (1982).
Fu et al., *The Veterinary Record*, (1989).
Fukuhara et al., *Archives of Virology*, 97:93–99, (1987).
Grunert et al., *The Journal of Infectious Diseases*, vol. 136. No. 2, (Aug., 1977).
Honda et al., *Jpn. J. Vet. Sci.* 52(1):49–54, (1990).
Knowles et al., *Archives of Virology*, 62, 201–208, (1979).
Kusanagi et al., *J. Vet. Med. Sci.*, 54(2):313–318, (1992).
Mettenleiter et al., *Archives of Virology*, 179, 498–503, (1990).
Potts et al., *Journal of Virological Methods*, 26 119–124, (1989).
Roth et al., *Cell*, vol. 33 435–443, (1983).
Roth et al., *The Journal of Cell Biology*, vol. 104, 769–782 (Mar., 1987).
Shaw et al., *Am. J. Vet. Res.*, vol. 50, No. 11, (Nov., 1989).
A. Smith et al., *Nature*, vol. 244, (Jul. 13, 1973).
Bautista et al., *J. Vet. Diagn. Invest.*, 5:612–614, (1993).
Carvajal et al., *J. Vet. Diagn. Invest.*, 7:60–64, (1995).
Meng et al., *J. Vet. Diagn. Invest.*, 8:374–381, (1996).
Murtaugh et al., Allen D. Leman Swine Conference, (1997).
Seal et al., *J. Vet. Diagn. Invest.*, 7:190–195, (1995).
Seal et al., *Virus Research*, 37, 1–12, (1995).
Yuan et al., American Society for Virology, 16th Annual Meeting, Bozeman Montana, (Jul. 19–23, 1997).
Decision (dated Oct. 26, 1999) in Civil Action No. 98–5703(HAA) relating to U.S. Patent No. 5,840,563.
Plaintiff's (Boehringer Ingelheim Vetmedica et al.) Post–Hearing Brief dated Sep. 10, 1999 from Civil Action No. 98–5703(HAA).
Defendant's (Schering–Plough Corp. et al.) Post–Hearing Brief dated Sep. 10, 1999 from Civil Action No. 98–5703(HAA).
Defendant's (Schering–Plough Corp. et al.) Critique of Plaintiff's (Boehringer Ingelheim Vetmedica et al.) Findings of Fact and Conclusions of Law dated Aug. 27, 1999 from Civil Action No. 98–5703(HAA).
Plaintiff's (Boehringer Ingelheim Vetmedica et al.) Critique of Defendant's (Schering–Plough Corp. et al.) Findings of Fact and Conclusions of Law dated Aug. 27, 1999 from Civil Action No. 98–5703(HAA).
Trial Testimony of Dr. Bernard Easterday dated Jun. 14, 1999 from Civil Action No. 98–5703(HAA).
Trial Testimony of Dr. Michael Murtaugh dated Jun. 18, 1999 from Civil Action No. 98–5703(HAA).
Trial Testimony of Drs. Bernard Easterday and Richard Steece dated Jun. 22, 1999 from Civil Action No. 98–5703(HAA).
Trial Testimony of Dr. Richard Steece and Mr. George Gould dated Jun. 23, 1999 from Civil Action No. 98–5703(HAA).
Trial Testimony of Dr. Raymond Rowland and Mr. Harry Manbeck dated Jun. 24, 1999 from Civil Action No. 98–5703(HAA).

(List continued on next page.)

*Primary Examiner*—Ali Salimi
*Attorney, Agent, or Firm*—Foley & Lardner

[57] ABSTRACT

The invention includes a vaccine and sera for treatment of Mystery Swine Disease (MSD), a method for producing the vaccine, methods for diagnosis of MSD, a viral agent that will mimic "mystery swine disease" and antibodies to the viral agent useful in diagnosis and treatment of MSD. The serum contains mammalian antibodies which are effective in treating MSD.

13 Claims, 5 Drawing Sheets

OTHER PUBLICATIONS

Trial Testimony of Mr. Harry Manbeck dated Jun. 25, 1999 from Civil Action No. 98–5703(HAA).

Defendant's (Schering–Plough Corp. et al.) Memorandum dated Mar. 18, 1999 in Opposition to Plaintiff's (Boehringer Ingelheim Vetmedica et al.) Motion for Preliminary Injuction from Civil Action No. 98–5703(HAA), including the Declaration of Dr. Raymond as Exhibit 1.

Defandant's (Schering–Plough Corp. et al.) Opposition to Plaintiff's Motion for Preliminary Injuction from Civil Action No. 96–04047(HAA) dated Jan. 21, 1997 (Redacted Public Copy).

Declaration of Dr. Richard Steece in connection with Defendant's Opposition from Civil Action No. 96–04047(HAA).

Expert Report of Dr. Richard Steece, Ph.D., SM (AAM) dated Cct. 2, 1998 from Civil Action No. 96–04047(HAA).

Supplemental Expert Report of Dr. Richard Steece, Ph.D., SM (AAM) dated Oct. 5, 1998 from Civil Action No. 96–04047(HAA).

Expert Report of Harry F. Manbeck, Jr. dated Oct. 5, 1998 from civil Action No. 96–04047(HAA).

Rebuttal Expert Report of Harry F. Manbeck, Jr. dated Oct. 26, 1998 from Civil Action No. 96–04047(HAA).

Defendant's Memorandum in Support of Motions for Summary Judgment from Civil Action No. 96–04047(HAA). (non–confidential copy) dated Jan. 5, 1998.

Defendant's Reply Brief in Opposition to Plaintiff's (Boehringer Ingelheim Animal Health, Inc.) Cross–Motions for Preliminary Injunction and Summary Judgment from Civil Action No. 96–04047(HAA) dated Mar. 6, 1998 (Redacted).

Declaration of Dr. Raymond Rowland from Civil Action No. 96–04047(HAA) in connection with Defendant's Reply Brief (Redacted).

Plaintiff's Critique of Defendant's Proposed Findings of Fact and Conclusions of Law from Civil Action No. 96–04047(HAA) dated Aug. 18, 1997 (Redacted).

Defendant's Critique of Plaintiff's Findings of Fact and Conclusions of Law from Civil Action No. 96–04047(HAA) dated Aug. 18, 1997 (Redacted).

Trial testimony of Mr. Danny Chladek dated Jun. 11–13, 1997 from Civil Action No. 96–04047(HAA) (Redacted).

Trial testimony of Dr. Michael Murtaugh dated Jun. 13 and 16, 1997 from Civil Action No. 96–04047(HAA) (Redacted).

Trial testimony of Dr. Edward Dubovi dated Jun. 16–17, 1997 from Civil Action No. 96–04047(HAA) (Redacted).

Trial testimony of Dr. Robert Rowland dated Jun. 19, 1997 from Civil Action No. CIV 96–04047(HAA) (Redacted).

Defendant's (Bayer Corp.) Initial Expert Disclosures from Civil Action No. 97–2508–JWL dated Aug. 14–17, 1998.

T.A. Axenova et al., "Propagation of Rabies Vaccine Virus in Continuous Green Monkey Kidney Cells 4647," (1984).

N. Burroughs et al., *Intervirology,* 10:51–59, (1978).

S. Chutivongse et al., *Vaccine,* vol. 9, pp. 573–576, (Aug., 1991).

Peter W. Mason, *Virology,* 169, 354–364, (1989).

B.J. Montagnon, *Develop. Biol. Standard.,* vol. 70, pp. 27–47, (1989).

C. Nishimura et al., *Japan. J. Microbiol.,* vol. 15(4), pp. 309–316, (1971).

Bautista et al., 1993, Comparison of Porcine Alveolar Macrophages and C1 2621 for the Detection of Porcine Reproductive and Respiratory Syndrome(PRRS) Virus and Anti–PRRS Antibody, *J Vet Diagn Invest,* 5:163–165.

Collins et al., 1998, Swine Diagnostic Pathology, 1998 Allen D. Leman Swine Conference, 1–5.

Mengeling et al., 1996, Comparison Among Strains of Porcine Reproductive and Respiratory Syndrome Virus for Their Ability to Cause Reproductive Failure, *Am J Vet Res,* 57:834–839.

Wesley et al., 1996, Differentiation of Vaccine (Strain Resp-PRRS®) and Field Strains of Porcine Reproductive and Respiratory Syndrome Virus by Restriction Enzyme Analysis, *American Association of Swine Practitioners,* 141–143.

Yoon et al., 1994, A Modified Serum Neutralization Test for the Detection of Antibody to Porcine Reproductive and Respiratory Syndrome Virus in Swine Serum, *J Vet Diagn Invest,* 6:289–292.

Yoon et al., 1995, Failure to Consider the Antigenic Diversity of Porcine Reproductive and Respiratory Syndrome (PRRS) Virus Isolates May Lead to Misdiagnosis, *J Vet Diagn Invest,* 7:388–387.

Ashworth et al., 1979, Antibody–Dependent Cell–Mediated Cytotoxicity (ADCC) in Aujeszky's Disease, *Arch. Virol.,* 59:307–318.

Backstom et al., 1982, Respiratory Diseases of Swine, *Veterinary Clinics of North America: Large Animal Practice,* 4:259–276.

Boehringer Ingelheim Animal Health, Inc. v. Schering–Plough Corporation and Schering Corporation, No. CIV. 96–04047(HAA); Oct. 6, 1997; 984 F.Supp. 239.

Boehringer Ingelheim Animal Health, Inc. v. Schering–Plough Corporation and Schering Corporation, No. CIV. 96–04047(HAA); Apr. 27, 1998; 6 F.Supp 239.

Bruner et al., 1973, Hagan's Infectious Diseases of Domestic Animals, Cornell University Press, Table XXXII.

Caeiro et al., 1990, In Vitro DNA Replication by Cytoplasmic Extracts from Cells Infected with African Swine Fever Virus, *Virol.,* 179:87–94.

Chasey et al., 1986, Replication of A–typical Ovine Rotavirus in Small Intestine Cell Culture, *J. Gen. Virol.,* 67:567–576.

Clark et al., 1981, Trypsin Enhancement of Rotavirus Infectivity: Mechanism of Enhancement, . Virol., 39:816–822.

Conner et al., 1984, Isolation and Characteristics of an Equine Reovirus Type 3 and an Antibody Prevalence Survey to Reoviruses in Horses Located in New York State, Vet. Microbiol., 9:15–25.

Corn et al., 1990, Isolation of Vesicular Stomatitis Virus New Jersey Serotype from Phlebotomine Sand Flies in Georgia, Am, J. Trop. Med. Hyg., 42:476–482.

Dea et al., 1991, Isolation of Encephalomycocarditis Virus Among Stillborn and Post–weaning Pigs in Quebec, Arch. Virol., 117:121–128.

Dea et al., Virus Isolations From Farms in Quebec Experiencing Severe Outbreaks of Respiratory and Reproductive Problems, Proceedings Mystery Swine Disease Committee Meeting, Oct. 6, 1990, pp. 67–71.

delVal et al., 1986, Glycosylated Components of African Swine Fever Virus Particles, *Virol.,* 152:39–49.

Ehresmann et al., 1977, RNA Synthesized in Calicivirus—Infected Cells Is Atypical of Picornaviruses, *J. Virol.,* 22:572–576.

Enjuanes et al., 1976, Isolation and Properties of DNA of African Swine Fever (ASF) Virus, J. Gen. Virol., 32:479–492.

Estes et al., 1979, Simian Rotavirus SA 11 Replication on Cell Cultures, *J. Virol.,* 31:810–815.

Ferrari et al., 1986, Isolation of Cytopathic Strains of Rotavirus from Pigs, *Microbiologica,* 9:287–294.

Geisbert et al., 1990, Use of Immunoelectron Microscopy to Show Ebola Virus During the 1989 United Stated Epizootic, *J. Clin. Path.,* 43:813–816.

Hedger et al., 1989, Swine Vesicular Disease Virus, *Virus Infections of Porcines,* Elsevier Science Publishers B.V., 241–250.

Hofmann et al., 1989, Quantitation, Biological and Physicochemical Properties of Cell Culture—Adapted Porcine Epidemic Diarrhea Coronavirus (PEDV), *Vet. Microl.,* 20:131–142.

Hoshino et al., 1983, Isolation and Characterization of an Equine Rotavirus, *J. Clin. Microbiol.,* 18:585–591.

Hoshino et al., 1984, Serotypic Similarity and Diversity of Rotaviruses of Mammalian and Avian Origin as Studied by Plaque–Reduction Neutralization, *J. Infect. Dis.,* 149:694–702.

Jackwood et al., 1987, Replication of Infectious Bursal Disease Virus in Continuous Cell Lines, *Avian Diseases,* 31:370–375.

Kang et al., 1986, Primary Isolation and Identification of Avian Rotaviruses from Turkeys Exhibiting Signs of Clinical Enteritis in a Continuous MA–104 Cell Line, *Avian Diseases,* 30:494–499.

Kasza et al., 1970, Isolation and Characterization of a Reovirus from Pits, *Vet. Rec.,* 87:681–686.

Kouvelos et al., 1984, Comparison of Bovine, Simian and Human Rotavirus Structural Glycoproteins, *J. Gen. Virol.,* 65:1211–1214.

Madin, S.H., 1989, Vesicular Exanthema Virus, *Virus Infections of Porcines,* Elsevier Science Publishers B.V., 268–271.

Makable et al., 1986, Hemagglutination With Ovine Rotaviru, *Arch. virol.,* 90:153–158.

Mukamoto et al., 1991, Immunogenicity in Aujeszky's Disease Virus Structural Glycoprotein gVI (gp 50) in Swine, *Vet. Microbiol.,* 29:109–121.

Murphy et al., 1990, Virus Taxonomy, *Virology,* Raven Press, Ltd., 9–35.

Myers et al., 1989, Propagation of Avian Rotaviruses im Primary Chick Kidney Cell and MA–104 Cell Cultures, *Avian Diseases,* 35:578–581.

Roberts, S.J., 1986, Abortion in Swine, *veterinary Obstetrics and Genital Diseases,* Edwards Brothers, Inc., Ann Arbor, 180–192.

Saif et al., 1988, Serial Propagation of Porcine Group C Rotavirus (Pararotavirus) in a Continuous Cell Line and Characterization of the Passage Virus, *J. Clin. Microbiol.,* 26:1277–1282.

Tauraso et al., 1968, Simian Hemorrhagic Fever, III Characterization of a Viral Agent, *Am. J. Trop. Med. Hyg.,* 17:422–431.

Theil et al., 1988, Partial Characterization of a Bovine Group A Rotavirus with a Short Genome Electropherotype, *J. Clin. Microbiol.,* 26:1094–1099.

Thouless et al., 1986, Isolation of Two Lapine Rotaviruses: Characterization of Their Subgroup, Serotype and RNA Electropherotypes, *Arch. Virol.,* 89:161–170.

Tsunemitsu et al., 1991, Isolation Characterization and Serial Propagation of a Bovine Group C Rotavirus in a Monkey Kidney Cell Line (MA–104), *J. Clin. Microbiol.,* 29:2609–2613.

Van Alstine, Past Diagnostic Approaches and Findings and Potentially Useful Diagnostic Strategies, Proceedings Mystery Swine Disease Committee Meeting, Oct. 6, 1990, pp. 52–58.

Beghi, E. et al., 1985, Guillain–Barre Syndrome, Clinicoepidemiologic Features and Effect of Influenza Vaccine, *Arch. Neurol,* 42:1053–1057.

Garwes, D.J., 1988, Transmissible gastroenteritis, *Veterinary Record,* 122:462–463.

Grouse, L.D., 1980, Swine Flue Sequelae, *JAMA,* 243(24)2489.

Just, M. et al., 1978, 76 Influenza Vaccine Trial in Serenegative Schoolchildren: Comparison of a Subunit Vaccine with a Whole–Virus Vaccine, *Med. Microbiol. Immunol.,* 164:277–284.

Masurel, N., 1976, Swine Influenza Virus and the Recycling of Influenza–A Viruses in Man, *The Lancet,* 244–247.

McKinney, W.P., 1990, Fatal Swine Influenza Pneumonia During Late Pregnancy, *Arch Intern Med.,* 150:213–215.

Poser, C.M., 1985, Swine Influenza Vaccination, *Arch Neurol,* 42:1090–1092.

Seneca, H., 1980, Influenza: Epidemiology, Etiology, Immunization and Management, *Journal of the American Geriatrics Society,* vol. XXVIII(6):241–250.

Shope, R.E. et al., 1936, The Susceptibility of Swine to the Virus of Human Influenza, Annual Meeting of the Society of American Bacteriologists in New York,, pp. 791–801.

Shortridge, K.F. et al., 1979, Geographical Distribution of Swine (HSw1N1) and Hong Kong (H3N2) Influenza Virus Variants in Pigs in Southeast Asia, *Intervirology,* 11:9–15.

Thomson, G. et al., 1991, Proliferative and necrotizing pneumonia (PNP) of swine: the Ontario Situation, *Can Vet J.,* 32:313.

Benfield, D. A. et al., Characterization of swine infertility and respiratory syndrome (SIRS) virus (isolate ATCC VR–2332), *J. Vet. Diagn. Invest.,* vol. 4, pp. 127–133 (Apr. 1992—4th week).

Benfield, D. et al., "Properties of SIRS Virus Isolate ATCC VR–2332 in the United States and Preliminary Characterizaiton of a Monoclonal Antibody to this Virus," *American Association of Swine Practitioners Newsletter,* vol. 4, No. 4, pp. 19–20, (Jul./Aug. 1992, normally marked first week of month, (i.e. Jul.).

Christianson, W. T., "Experimental reproduction of swine infertility and respiratory syndrome in pregnant sows," *Am. J. Vet. Res.,* vol. 53, No. 4, pp. 485–488 (Apr. 1992).

Collins, J.E., et al., "Isolation of swine infertility and respiratory syndrome virus (isolate ATCC VR–2332) in North America and experimental reprodution of the disease in gnotobiotic pigs," *J. Vet. Diagn. Invest.,* vol. 4, pp. 117–126 (Apr. (4th week) 1992).

Cooper, V.L., et al., "Porcine reproductive and respiratory syndrome: NEB–1 PRRSV infection did not potentiate bacterial pathogens," *J. Vet. Diagn. Invest.,* vol. 7, pp. 313–320 (1995).

Dea, S. et al., "Antigenic variant of swine influenza virus causing proliferative and necrotizing pneumonia in pigs," *J. Vet. Diagn. Invest.,* vol. 4, pp. 380–392 (Oct. 1992).

Drew, T., Porcine Reproductive and Respiratory Syndrome Virus: A Review, 3 pages (Apr. 1996).

Morrison, R. B. et al., "Brief Communications," *J. Vet. Diagn. Invest.,* vol. 4, pp. 186–188 (Apr. 1992).

Kapur, V., "Genetic variation in porcine reproductive and respiratory syndrome virus isolates in the midwestern United States," *Journal of General Virology*, vol. 77, pp. 1271–1276 (1996).

Murtaugh, M. P., et al., "Comparison of the structural protein coding sequences of the VR–2332 and Lelystad virus strains of the PRRS virus," *Arch. Virol.*, vol. 140, pp. 1451–1460, (1995).

Ojeh, C.K. et al., "Isolation, Characterisation and Serial Propagation of a Nigerian Strain of Porcine Group A Rotavirus in a Monkey Kidney Cell Line (MA104)," *Discov. Innov.*, vol. 8, No. 2, pp. 159–164 (Apr. 1995).

Wensvoort, G. et al., "Antigenic comparison of Lelystad virus and swine infertility and respiratory syndrome (SIRS) virus," *J. Vet. Diagn. Invest.*, vol. 4, pp. 134–138 (Apr. 1992).

Wieczorek–Krohmer, M. et al., "Porcine reproductive and respiratory syndrome virus (PRRSV): Monoclonal antibodies detect common epitopes on two viral proteins of European and U.S. Isolates," *Veterinary Microbiology*, vol. 51, pp. 257–266 (1996).

Yoon, J. et al., "Isolation of a cytophathic virus from weak pigs on farms with a histroy of swine infertility and respiratory syndrome," *J. Vet. Diagn. Invest.*, vol. 4, pp. 139–143 (Apr. 1992).

P. Halbur et al., Conference of Research Workers in Animal Diseases; Abstracts of Papers; Chicago, Illinois; Nov. 1993; Paper 222.

R. Bilodeau et al., "'Porcine Reproductive and Respiratory Syndrome' in Quebec", *The Veterinary Record*, p. 102 (Aug. 3, 1991).

W. T. Christianson et al., "Swine Infertility and Respiratory Syndrome", *Pig Veterinary Journal*, 27, 9 (Apr. 1991).

J. E. Collins et al., "Respiratory Disease in a Swine Herd Experiencing A Reproductive Failure Syndrome", Minnesota Swine Conference for Veterinarians, p. 254 (Sep. 16–18, 1990).

J. E. Collins et al., "Experimental Transmission of Swine Reproductive Failure Syndrome (Mystery Swine Disease) in Gnotobiotic Piglets", 71st Annual Meeting of the Conference of Research Workers in Animal Disease, Chicago, IL (Nov. 5 & 6, 1990), Abstract No. 2.

J. E. Collins et al., "Swine Infertility and Respiratory Syndrome (Mystery Swine Disease)", Minnesota Swine Conference for Veterinarians (Sep. 16, 1991).

K. K. Keffaber, "Reproductive Failure of Unknown Etiology", *ASAP Newsletter*, 1 (Sep.–Oct. 1989).

K. K. Keffaber, "Swine Reproductive Failure of Unknown Etiology", The George A. Young Swine Conference & Annual Nebraska SPF Swine Conference, p. 55 (Aug. 13–14, 1990).

T. Loula, "Mystery Pig Disease", *Agri–Practice*, 12, 23 (Jan./Feb. 1991).

J. M. A. Pol et al., "Pathological, Ultrastructural, and Immunohistochemical Changes Caused by Lelystad Virus in Experimentally Induced Infections of Mystery Swine Disease (Synonym: Porcine Epidemic Abortion and Respiratory Syndrom (Pears))", *The Veterinary Quarterly*, 13, 137 (Jul. 1991).

C. Terpstra et al., "Experimental Reproduction of Porcine Epidemic Abortion and Respiratory Syndrome (Mystery Swine Disease) by Infection With Lelystad Virus: Koch's Postulates Fulfilled", *The Veterinary Quarterly*, 13, 131 (Jul. 1991).

W. G. Van Alstine, "Mystery Swine Disease in the United States", Workshop/Seminar on the "New" Pig Disease In the European Community (Apr. 29–30, 1991).

G. Wensvoort et al., M. White, "'Blue Ear' Disease of Pigs", *The Veterinary Record*, 128, 574 (Jun. 15, 1991).

G. Wensvoort et al., "Mystery Swine Disease in the Netherlands: the Isolation of Lelystad Virus", *The Veterinary Quarterly*, 13, 121 (Jul. 1991).

K. H. Witte, "The Situation of 'Epidemic Late Abortion of Swine' in the State of Northrhine–Westphalia", Workshop Seminar (Apr. 1991).

*Animal Pharm.*, No. 228, p. 2 (May 24, 1991).

"Blue–Eared Disease Suspected in Two More Counties", *The Veterinary Record*, 129 (Jul. 6, 1991).

Proceedings of the Mystery Swine Disease Committee Meeting, Denver, CO (Oct. 6, 1990).

D. A. Benfield et al., "Etiologic Agent of Swine Infertility and Respiratory Syndrome in the United States", 72st Annual Meeting of the Conference of Research Workers in Animal Disease, Chicago, IL (Nov. 11 & 12, 1991), p. 48, Abstract No. 268.

W. T. Christianson et al., "Experimental Reproduction of a Newly Described Viral Disease, Swine Infertility and Respiratory Syndrome (SIRS), in Pregnant Sows", 72st Annual Meeting of the Conference of Research Workers in Animal Disease, Chicago, IL (Nov. 11 & 12, 1991), p. 48, Abstract No. 269.

J. E. Collins, "Newly Recognized Respiratory Syndromes in North American Swine Herds", *American Association of Swine Practitioners Newsletter*, 3, 7 (Sep.–Oct., 1991).

R. B. Morrison et al., "Sero–epidemiologic Investigation of Swine Infertility and Respiratory Syndrome (SIRS)", 72st Annual Meeting of the Conference of Research Workers in Animal Disease, Chicago, IL (Nov. 11 & 12, 1991), p. 55, Abstract No. 309.

T. Quaife, "Mystery Agent Isolated!", *Swine Practitioner*, p. 4 (Nov. 1991).

F.–W. von Busse, Epidemiologic Studies on Porcine Reproductive and Respiratory Syndrome (PRRS), *Tier rztliche Umschau*, p. 708 (Dec. 1991) (Abstract in English—p. 711).

V. F. von Ohlinger, Aetiological Studies of the Porcine Reproductive and Respiratory Syndrome (PRRS), *Tier rztliche Umschau*, p. 703 (Dec. 1991) (Abstract in English—p. 703).

Porcine Reproductive and Respiratory Syndrome: A Report on the Seminar Held in Brussels on 4–5 Nov. 1991 and Organized by the European Commission.

Dacso, C.C. et al., "Sporadic Occurrence of Zoonotic Swine Influenza Virus Infections", *Journal of Clinical Microbiology*, 20(4): 833–835 (Oct. 1984).

Beare et al., "Further Studies in Man of Hsw1N1 Influenza Viruses," *Journal of Medical Virology*, 5:33–38 (1980).

Berendt et al., "Evaluation of Commercially Prepared Vaccines for Experimentally Induced Type/A/New Jersey/8/76 influenza Virus Infections in Mice and Squirrel Monkeys," *The Journal of Infectious Disease*, vol. 136, pp. S712–S718, Supplement (1977).

Berendt et al., "Reaction of Squirrel Monkeys to Intratracheal Inoculation with Influenza/A/New Jersey/76 (Swine) Virus," *Infection and Immunity*, pp. 476–479 (1977).

Bohl et al., "Isolation and Serotyping of Porcine Rotaviruses and Antigenic Comparison with Other Rotaviruses," *Journal of Clinical Microbiology*, pp. 105–111, (1984).

Bouillant et al., "Viral Susceptibility of a Cell Line Derived from the Pig Oviduct," *Can. J. comp. Med.,* vol. 39, pp. 450–456, (1975).

Cabasso et al., "Propagation of Infectious Canine Hepatitis Virus in Tissue Culture. (20843)," *P.S.E.B.M.,* v85, pp. 239–245, (1954).

Callebaut et al. "Antigenic Differentiation between Transmissible Gastroenteritis Virus of Swine and a Related Porcine Respiratory Coronavirus," *J. gen. Virol.,* 69, 1725–1730, (1988).

Charley, "Interaction of Influenza Virus With Swine Alveolar Macrophages: Influence of anti–virus Antibodies and Cytochalasin B," *Ann. Virol. (Inst. Pasteur),* 134 E, 51–59, (1983).

Dea et al., "Antigentic Variant of Swine Influenza Virus Causing Proliferative and Necrotizing Pneumonia in Pigs," *J. Vet. Diagn. Invest.,* vol. No. 4, pp. 380–392 (Apr. 1992).

Dea et al., "Caractéristiques d'isolates des virus influenza et de l'encéphalomyocardite associés au Syndrome Reproducteur et Respiratoire Porcin (S.R.R.P.) au Québec$^a$," *Le Médecin Vétérinaire Du Québec,* vol. 21, No. 4, pp. 170–175, (Nov. 1991). A copy of an English translation is attached.

Derbyshire, J.B., "Porcine Enterovirus Infections", *Diseases of Swine,* Fifth Edition, Chapter 20: 265–270 (1958).

Easterday, "Swine Influenza," *Diseases of Swine,* 6th Edition, pp. 244–255, (1986).

Girard, et al., "Experimentally Induced Porcine Proliferative and Necrostising Pneumonia with an Influenza A Virus," *The Veterinary Record,* (1992) 130, 206–207, Mar. 7, 1992.

Goldfiend, M. et al., "Influenza in New Jersey in 1976: Isolations of Influenza A/New Jersey/76 Virus at Fort Dix" *Journal of Infectious Disease* 136 Supp.: S347–S355 (1977).

Goldstein, M.A et al., "Evaluation of Three Cell Culture Systems as Substrates for Influenza Virus Assay", *Applied Microbiology,* 19(4): 580–582 (1970).

Gourreau et al., "Diffusion Du Virus De La Grippe Du Porc (H1N1 = Hsw1N1) En France," *Ann. Virol. (Inst. Pasteur),* 132 E, 287–294 (1981).

Graves, J.H., "Swine Vesicular Disease", *Diseases of Swine,* Fifth Edition, Chapter 23: 288–293 (1958).

Grizzard et al., "Experimental Production of Respiratory Tract Disease in Cebus Monkeys After Intratracheal or Intranasal Infection with Influenza A/Victoria/3/75 or Influenza A/New Jersey/76 Virus," *Infection and Immunity,* vol. 21, No. 1, pp. 201–205, (1978).

Gustafson, D.P., "Pseudorables", *Diseases of Swine,* Fifth Edition, Chapter 14: 209–223 (1958).

Heath, R.B. et al., "The Behaviour of Some Influenza Viruses in Tissue Cultures of Kidney Cells of Various Species", *Archiv. f. Virusforschung Bd. VIII,* HS: 577–591 (1958).

Hofmann, M. et al., "Propagation of the Virus of Porcine Epidemic Diarrhea in Cell Culture", *Journal of Clinical Microbiology,* 26(11): 2235–2239 (1988).

Imagawa et al., "Isolation of Foal Rotavirus in MA–104 Cells," *Bull. Equine Res. Inst.,* No. 18, 119–128 (1981).

Johnson, "Feline Panleucopaenia Virus: IV.—Methods for Obtaining Reproducible in vitro Results," *Res. vet. Sci.,* 8, pp. 256–265, (1967).

Kundin, "Hong Kong A–2 Influenza Virus Infection among Swine during a Human Epidemic in Taiwan," *Nature,* vol. 228, p. 857 and cover page.

Madec et al., "Consequences Pathologiques D'un Episode Grippal Severe (Virus Swine A/$H_1N_1$) Dans Les Conditions Naturelles Chez La Truie Non Immune En Debut De Gestation," *Comp. Immun. Microbiol. infect. Dis.,* vol. 12, No. 1/2, pp. 17–27, (1989).

McDaniel, H.A., "African Swine Fever", *Diseases of Swine,* Fifth Edition, Chapter 16: 237–245 (1958).

McFerran, J.B., "Reovirus Infection" *Diseases of Swine,* Fifth Edition, Chapter 28: 330–336 (1958).

McIntosh, "Diagnostic Virology," Chapter 17 of *Fields Virology,* Second Edition, vol. 1, pp. 411–437, (1990).

McQueen, J.L.. et al., "Influenza in Animals", *Advances in Veterinary Science,* 12:285–337 (1968).

Meikeljohn et al., "Respiratory Virus Vaccine Evaluation and Surveillance," *Semi–Annual Contract Progress report to the National Institute of Allergy and Infectious Diseases,* 21 pgs., (Sep. 15, 1965 to Mar. 15, 1966).

Moore, C., "Porcine Proliferative and Necrotyzing Penumonia Clinical Findings," Presented at American Association of Swine Practitioners, 22nd Annual Meeting, pp. 443–453 (Mar. 3–5, 1991).

Morin et al., "Severe proliferative and necrotizing pneumonia in pigs: A newly recognized disease," *Can Vet J,* vol. 31, pp. 837–839 (Dec. 1990).

Murakami et al., "Difference in growth behavior of human, swine, equine, and avian influenza viruses at a high temperature," *Arch Virol,* 100: 231–244 (1988).

Nakamura et al., "Studies on Swine Influenza. III. Propagation of Swine Influenza Virus in Explants of Respiratory Tract Tissues from Fetal Pigs," *Studies on Swine Influenza,* pp. 27–35, (1968).

Pan, I.C. et al., "Replication of African Swine Fever Virus in Cell Cultures", *Am J Vet Res.,* 41(9): 1357–1367 (1980).

Patriarca, P.A. et al., "Lack of Significant Person–to–Person Spread of Swine Influenza–Like Virus Following Fatal Infection in an Immunocompromised Child", *American Journal of Epidemiology,* 119(2): 152–158 (1984).

Pirtle et al., "Morphologic Heterogeneity of a Strain of Swine Influenza Virus (A/Swine/Wisconsin/1/68, Hsw1N1) Propagated at Different Temperatures," *Am J Vet Res,* vol. 36, No. 1, pp. 1783–1787 (1975).

Polson et al., "Financial Implications of Mystery Swine Disease (MSD)," Livestock Conservation Institute Proceedings, Mystery Swine Disease Committee Meeting, pp. 8–27, Oct. 6, 1990.

Potgieter et al., "Isolation of Swine Influenza Virus in Oklahoma," *JAVMA,* vol. 171, No. 8, pp. 758–760, (1977).

Reed et al., "Persistent Respiratory Virus Infection in Tracheal Organ Cultures," *Br. J. exp. Path.,* 50, 378–388, (1969).

Schmidt et al., "Infection by Influenza A Viruses of Tracheal Organ Cultures Derived from Homologous and Heterologous Hosts," *The Journal of Infectious Diseases,* vol. 129, No. 1, pp. 28–36, (1974).

Smith, T.F. et al., "Isolation of Swine Influenza Virus From Autopsy Lung Tissue of Man", *New England Journal of Medicine:* 708–710 (Mar. 25, 1976).

Stephen et al., "Swine Influenza Virus Vaccine: Potentiation in Rhesus Monkeys in Antibody Responses by a Nuclease Resistant Derivative of Poly I–Poly C," U.S. Army Medical Research Institute of Infectious Diseases, Fort Detrick, Frederick, MD 21701, 12 pages (double–sided), (1976).

Stephen et al., "Swine Influenza Virus Vaccine: Potentiation of Antibody Responses in Rhesus Monkeys," pp. 1289–1290, (1977).

Stim, T.B., "Arbovirus Plaquing in Two Simian Cell Lines", *J. gen Virol.,* 5: 329–338 (1969).

Theil et al., "Isolation and Serial Propagation of Turkey Rotaviruses in a Fetal Rhesus Monkey Kidney (MA104) Cell Line," *Avain Diseases,* vol. 30, No. 1, pp. 93–104 (1985).

Tobita et al., "Plaque Assay and Primary Isolation of Influenza A Viruses in an Established Line of Canine Kidney Cells (MDCK) in the Presence of Trypsin," *Med. Microbiol. Immunol.,* 162, 9–14 (1975).

Travassos da Rosa, A.P. et al., "Carajas and Maraba Viruses, Two New Vesiculoviruses Isolated From Phlebotomine Sand Flies in Brazil", *Am J. Trop. Med. Hyg.,* 33(5): 999–1006 (1984).

Urasawa et al., "Sequential Passages of Human Rotavirus in MA–104 Cells," *Microbiol. Immunol.,* vol. 25 (10), 1025–1035, (1981).

van Nieuwstadt et al., "Infection with porcine respiratory coronavirus does not fully protect pigs against intestinal transmissible gastroenteritis virus," *The Veterinary Record,* pp. 58–60, (1989).

van Nieuwstadt, et al., "Use of Two enzyme–linked immunosorbent assays to monitor antibody responses in swine with experimentally induced infection with porcine epidemic diarrhea virus," *Am. J. Vet. Res.,* 52, No. 7, pp. 1044–1050, (Jul. 1991).

Webster et al., "Chemotherapy and Vaccination: a Possible Strategy for the Control of Highly Virulent Influenza Virus," *Journal of Virology,* vol. 55, No. 1, pp. 173–176, (1985).

Woode, G.N. et al., "Porcine Rotavirus Infection", *Diseases of Swine,* Fifth Edition, Chapter 26: 310–322 (1958).

Woods et al., "Antigenicity of Inactivated Swine Influenza Virus Concentrated by Centrifugation," *Research Communications in Chemical Pathology and Pharmacology,* vol. 13, No. 1, pp. 129–132, (1976).

Woods et al., "Experimental Challenge of Pregnant Gilts with Swine Influenza Virus After Vaccination," *Research Communications in Chemical Pathology and Pharmacology,* vol. 15, No. 4, pp. 787–795, (1976).

Woods et al., "Investigation of Four Outbreaks of Acute Respiratory Disease in Swine and Isolation of Swine Influenza Virus," *Swine Influenza,* vol. 5, No. 4, H.L.S., pp. 218–224, (1968).

Yamane et al., "Annual Examination of Influenza Virus Infection Among Pigs in Miyagi Prefecture, Japan: The Appearance of Hsw1N1 Virus," *Acta. virol.,* 23: 240–248 (1979).

*Animal Pharm.,* 230, p. 21 (Jun. 21, 1991).

METHOD OF PRODUCING A VACCINE FOR SWINE INFERTILITY AND RESPIRATORY SYNDROME

This application is a continuation of U.S. Ser. No. 08/316,529 (filed Sep. 30, 1994; issued as U.S. Pat. No. 5,846,805), which is a division of U.S. Ser. No. 08/301,738 (filed Sep. 6, 1994; abandoned), which is a continuation of U.S. Ser. No. 07/860,444 (filed Mar. 30, 1992; abandoned), which is a continuation-in-part of U.S. Ser. No. 07/749,839 (filed Aug. 26, 1991; abandoned), and U.S. Ser. No. 07/760,713 (filed Sep. 16, 1991, abandoned).

BACKGROUND OF THE INVENTION

Since 1987, the swine-producing industry has been subjected to a devastating epidemic of an unknown disease, often referred to as "Mystery Swine Disease" [MSD, more recently referred to as "Swine Infertility and Respiratory Syndrome (SIRS)], because researchers have been unable to identify the causative agent. MSD has affected hundreds of thousands of swine throughout North America and Europe. Once one pig is infected with MSD, that one pig can spread the MSD to an entire herd within three to seven days. From 1987 to 1991, the swine industry has lost millions of dollars in revenue as a result of MSD. A recent study estimates that MSD causes a financial loss between $250 and $500 per inventoried sow.

MSD causes multiple symptoms in swine. The first symptom of MSD in a breeding herd of swine is usually anorexia and mild pyrexia. In addition, the herd animals may exhibit bluish discolorations in their skin, especially in their ears, teats, snout, and the frontal portions of their necks and shoulders. The affected skin may become irreparably damaged. However, the most devastating symptom of MSD is the reproductive failure that occurs in a breeding herd of swine. MSD causes sows to bear stillborn piglets; undersized, weak piglets with respiratory distress; or piglets which die before they are weaned. Other reproductive symptoms caused by MSD include early farrowing of piglets, a decrease in conception rates, failure in some sows to cycle, and a reduction in the total number of piglets found in a litter. It has been estimated that the number of pigs lost from reproductive failure is about 10 to 15 percent of the annual production of pigs.

Research has been directed toward isolating the causative agent of MSD. A number of potential bacterial pathogens have been isolated. However, the types of potential bacterial pathogens have varied between swine-producing farms. Viral investigation has included fluorescent antibody examination, electron microscopic investigation, and serology. These methods have failed to locate the causative agent of MSD. As a result, no one has yet developed a vaccine which can be used to treat MSD in the swine population.

Therefore, it is an objective of the invention to provide a vaccine and sera which, when administered to a breeding swine herd, will reduce the presence of MSD in their population. Another object is to provide a method of treating a population of swine with the vaccine to eradicate MSD from the swine population. Yet another object is to provide a method for diagnosis of MSD.

SUMMARY OF THE INVENTION

These and other objects are achieved by the present invention which is directed to a vaccine and sera for prevention and treatment of mystery swine disease and to a method for its diagnosis in swine.

The vaccine is derived from an infectious agent that will infect swine with mystery swine disease (MSD). The infectious agent is obtained from an inoculum of processed tissue of swine infected with the disease, preferably lung tissue. Preferably, the infectious agent is the product of an in vitro mammalian cell culture such as a simian cell line infected with the inoculum of the infected swine tissue. Preferably, the inoculum contains biological particles no greater than about 1.0 micron in size, more preferably 0.5 micron, most preferably no greater than 0.2 micron. It is also preferable that the inoculum has been neutralized with antibodies to common swine diseases.

According to the present invention, a tissue homogenate obtained from piglets in SIRS-affected herds consistently reproduced the respiratory and reproductive forms of SIRS when intranasally inoculated in gnotobiotic piglets and pregnant sows. Gnotobiotic piglets so inoculated with-either unfiltered or filtered (0.45, 0.22, or 0.1 $\mu$m) inoculum became anorectic and developed microscopic lung lesions similar to lesions seen in SIRS-affected herds. The same inoculum also caused reproductive effects identical to those seen in SIRS-affected herds. A viral agent has been recovered from the tissue homogenate. The viral agent causes a disease that mimics SIRS in piglets and pregnant sows. The viral agent has not yet been classified. However, the viral agent is a fastidious, non-hemagglutinating enveloped RNA virus. A viral agent causing SIRS has been deposited on Jul. 18, 1991 with the American Type Culture Collection 10801 University Boulevard Manassas, Va. 20110-2209under the accession number ATCC VR-2332.

The serum for treatment of infected swine carries mammalian antibodies to the MSD. It is obtained from the blood plasma of a mammal (non-swine and swine) pre-treated with the above-described infectious agent.

Alternatively, the serum is formulated from monoclonal antibodies to MSD produced by hybridoma methods.

The method for diagnosis of MSD is based upon the use of immunospecific antibodies for MSD. The method calls for combination of a filtered homogenate of a lung biopsy sample or a biopsy sample or similar samples (homogenate or biopsy) from other tissue and the immunospecific antibodies followed by application of a known detection technique for the conjugate formed by this combination. Immobilization or precipitation of the conjugate and application of such detection techniques as ELISA; RIA; Southern, Northern, Western Blots and the like will diagnose MSD.

According to the present invention, therapeutic and diagnostic methods employing antibodies to MSD involve monoclonal antibodies (e.g., IgG or IgM) to the above-described fastidious, non-hemagglutinating enveloped RNA virus. Exemplary antibodies include SDOW 12 and SDOW 17, deposited with the American Type Culture Collection on Mar. 27, 1992 with accession numbers HB 10996 and HB 10997, respectively).

BRIEF DESCRIPTION OF THE FIGURES

FIG. 1A: Non-infected, unstained cell monolayer.

DETAILED DESCRIPTION OF THE INVENTION

Figure 1A:
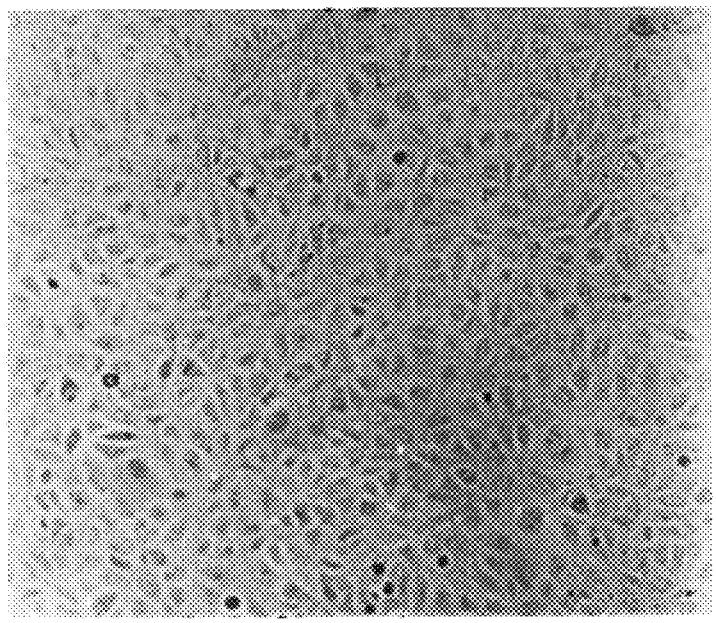
FIG. 1A shows a noninfected.

Determination of the cause of Mystery Swine Disease (MSD) has been difficult. According to the present invention, however, the isolation and growth of the infectious agent causing MSD has been achieved. As used herein, "infectious agent" refers to a virus capable of causing swine infertility and respiratory syndrome. More specifically, the infectious agent is a fastidious, non-hemagglutinating enveloped RNA virus and zoopathogenic mutants thereof capable of causing swine infertility and respiratory disease in swine. The isolation of the infectious agent is a major breakthrough and discovery. It enables the production of vaccines, antibody sera for treatment of infected swine, and diagnostic methods.

The vaccine is composed of an inactivated or attenuated MSD infectious agent, derived from an inoculum processed from infected swine lung tissue or other swine tissue exhibiting the characteristic lesions of MSD. Functional derivatives of infectious agent, including subunit, vector, recombinant, and synthetic peptide vaccines, or the like, are also envisioned. A multi-step procedure is utilized in developing the MSD vaccine. The MSD infectious agent is first obtained as an inoculum by separation and isolation from infected swine tissue, preferably the lung tissue. The MSD infectious agent is then treated using known vaccinological techniques to form a vaccine against MSD.

The MSD infectious agent is preferably isolated as an inoculate from lung tissue of pigs which exhibit rapid breathing due to the MSD (other tissue such as fetal tissue may also be used to recover virus). Such pigs are destroyed and their lung tissue removed. The lung tissue is then microscopically examined for thickened alveolar septae caused by the presence of macrophages, degenerating cells, and debris in alveolar spaces. These characteristics indicate the presence of the MSD infectious agent. Other swine tissue exhibiting lesions of this sort may also be used to isolate the MSD infectious agent.

The lung or other swine tissue is then homogenized with a pharmaceutically acceptable aqueous solution (such as physiological saline, Ringers solution, Hank's Balanced Salt Solution, Minimum Essential Medium, and the like) such that the tissue comprises 10 percent weight/volume amount of the homogenate. The homogenate is then passed through filters with pore diameters in the 0.05 to 10 micron range, preferably through a series-of 0.45, 0.2 and 0.1 micron filters, to produce a filtered homogenate containing the aMSD infectious agent. As a result, the filtered homogenate contains biological particles having a size no greater than about 1.0 micron, preferably no greater than about 0.2 to 0.1 micron. The filtered homogenate can then be mixed with Freund's incomplete adjuvant so that the production of antibodies can be stimulated upon injection into a mammal. This mixture can be used as an inoculum for development of MSD in swine or further study of the MSD infectious agent.

After obtaining a filtered homogenate containing the infectious agent, the infectious agent can be inactivated or killed by treatment of the filtered homogenate with a standard chemical inactivating agent such as an aldehyde reagent including formalin, acetaldehyde and the like; reactive acidic alcohols including cresol, phenol and the like; acids such as benzoic acid, benzene sulfonic acid and the like; lactones such as beta propiolactone and caprolactone; and activated lactams, carbodiimides and carbonyl diheteroaromatic compounds such as carbonyl diimidazole. Irradiation such as with ultraviolet and gamma irradiation can also be used to inactivate or kill the infectious agent. Alternatively, the infectious agent can be attenuated by its repeated growth in cell culture from non-swine mammal or avian origin so that the ability of the infectious agent to virulently reproduce is lost. The details of the cell culture attenuation technique are given below.

The killed or attenuated infectious agent is then diluted to an appropriate titer by addition of a diluent adjuvant solution for stimulation of immune response. The titration is accomplished by measurement against MSD antibody in an immunologic test such as an ELISA, RIA, IFA or enzyme substrate detection test as described below.

To produce a purified form of the infectious agent, the filtered homogenate described above can be inoculated into a series of in vitro cell preparations. Cell preparations with mammalian organ cells such as kidney, liver, heart and brain, lung, spleen, testicle, turbinate, white and red blood cells and lymph node, as well as insect and avian embryo preparations can be used. Culture media suitable for these cell preparations include those supporting mammalian cell growth such as fetal calf serum and agar, blood infusion agar, brain-heart infusion glucose broth and agar and the like. Preferably the mammalian cells are monkey kidney cells, most preferably African green monkey kidney embryonic cells—monkey kidney cell line (MA-104).

After inoculating the cell preparation with the filtered homogenate and growing the culture, individual clumps of cultured cells are harvested and reintroduced into sterile culture medium with cells. The culture fluid from the final culture of the series provides the purified form of the virulent infectious agent. Also, after a series of repeated harvests have been made, the culture can be grown, the culture fluid collected and the fluid used as an inoculum for a culture of a different cellular species. In this fashion, the infective agent can be attenuated such that the culture fluid from the differing species culture provides the purified form of the attenuated infectious agent.

Polyclonal antibody sera can be produced through use of the infectious agent as an antigenic substance to raise an immune response in mammals. The culture fluid or inoculum prepared as described above can be administered with a stimulating adjuvant to a non-swine mammal such as a horse, goat, mouse or rabbit. After repeated challenge, portions of blood serum can be removed and antigenically purified using immobilized antibodies to those disease specific antibodies typically found in the serum of the bled animal. Further treatment of the semi-purified serum by chromatography on, for example, a saccharide gel column with physiological saline and collection of proteinaceous components of molecular weight at least 10,000 provides a purified polyclonal sera for use in treatment.

Monoclonal antibody sera can be produced by the hybridoma technique. After immunization of a mouse, pig, rat, rabbit or other appropriate species with MSD containing cell culture lysate or gradient-purified MSD as described above, the spleen of the animal can be removed and converted into a whole cell preparation. Following the method of Kohler and Milstein (Kohler et al., Nature, 256, 495–97 (1975)), the immune cells from the spleen cell preparation can be fused with myeloma cells to produce hybridomas. Culturation of the hybridomas and testing the culture fluid against the fluid or inoculum carrying the infectious agent allows isolation of the hybridoma culture producing monoclonal antibodies to the MSD infectious agent. Introduction of the hybridoma into the peritoneum of the host species will produce a peritoneal growth of the hybridoma. Collection of the ascites fluid yields body fluid containing the monoclonal antibody to the infectious agent. Also, cell culture supernatant from the hybridoma cell culture can be used. Preferably the monoclonal antibody is produced by a murine derived hybrid cell line wherein the antibody is an IgG or IgM type immunoglobulin. Example monoclonal antibodies to the infectious agent for SIRS are monoclonal antibody SDOW 12 and SDOW 17. In addition to uses discussed elsewhere in this application, monoclonal antibodies according to the present invention can be employed in various diagnostic and therapeutic compositions and methods, including passive immunization and anti-idiotype vaccine preparation.

The vaccine of the present invention is capable of preventing and curing MSD infections found in the swine population. For effective prophylactic and anti-infectious use in vivo, the MSD vaccine contains killed or attenuated MSD infectious agent and may be administered alone or in combination with a pharmaceutical carrier that is compatible with swine. The vaccine may be delivered orally, parenterally, intranasally or intravenously. Factors bearing on the vaccine dosage include, for example, the age, weight, and level of maternal antibody of the infected pig. The range of a given dose is $10^3$ to $10^7$ Tissue Culture Infective Dose 50 per ml, preferably given in 1 ml to 5 ml doses. The vaccine doses should be applied over about 14 to 28 days to ensure that the pig has developed an immunity to the MSD infection.

The MSD vaccine can be administered in a variety of different dosage forms. An aqueous medium containing the killed or attenuated MSD infectious agent may be desiccated and combined with pharmaceutically acceptable inert excipients and buffering agents such as lactose, starch, calcium carbonate, sodium citrate formed into tablets, capsules and the like. These combinations may also be formed into a powder or suspended in an aqueous solution such that these powders and/or solutions can be added to animal feed or to the animals' drinking water. These MSD vaccine powders or solutions can be suitably sweetened or flavored by various known agents to promote the uptake of the vaccine orally by the pig.

For purposes of parenteral administration, the killed or attenuated MSD infectious agent can be combined with pharmaceutically acceptable carrier(s) well known in the art such as saline solution, water, propylene glycol, etc. In this form, the vaccine can be parenterally, intranasally, and orally applied by well-known methods known in the art of veterinary medicine. The MSD vaccine can also be administered intravenously by syringe. In this form, the MSD vaccine is combined with pharmaceutically acceptable aqueous carrier (s) such as a saline solution. The parenteral and intravenous formulations of MSD vaccine may also include emulsifying and/or suspending agents as well, together with pharmaceutically acceptable diluent to control the delivery and the dose amount of the MSD vaccine.

The method for diagnosis of MSD is carried out with the polyclonal or monoclonal antibody sera described above. Either the antibody sera or the biopsied tissue homogenate may be immobilized by contact with a polystyrene surface or with a surface of another polymer for immobilizing protein. The other of the antibody sera and homogenate is then added, incubated and the non-immobilized material removed, for example, by washing. A labeled species-specific antibody for the antibody sera is then added and the presence and quantity of label determined. The label determination indicates the presence of MSD in the tissue assayed. Typical embodiments of this method include the enzyme linked immunosorbent assay (ELISA); radioimmunoassay (RIA); immunofluorescent assay (IFA); Northern, Southern, and Western Blot immunoassay.

The following examples further illustrate specific embodiments of the invention. The examples, however, are not meant to limit the scope of the invention which has been fully characterized in the foregoing disclosure.

EXAMPLE 1

The MSD infectious agent may be characterized by determining physiochemical properties (size, sensitivity to lipid solvents, and sensitivity to protease) by treatment of the inoculum followed by the inoculation of gnotobiotic pigs to determine if the MSD infectious agent remains pathogenic.

A. Materials

Gnotobiotic Pigs

Derivation and maintenance procedures for gnotobiotic pigs have been described in Benfield et al., Am. J. Vet. Res., 49, 330–36 (1988) and Collins et al., Am. J. Vet. Res., 50, 824–35 (1989). Sows can be obtained from a herd free of reproduction problems including MSD. Litters with stillborn and/or mummified fetuses should not be used.

MSD Inoculum (MN90-SD76-GP2, Referred to Herein as MNSD90x76-L or MNSD90x76-P)

Trachea, lung, turbinates, tonsil, liver, brain, and spleen can be collected from nursing pigs in a Minnesota swine herd spontaneously infected with MSD (Collins et al., Minnesota Swine Conference for Veterinarians, Abstract, 254–55 (1990)). A homogenate of these tissues (designated MN 89-35477) has been prepared in Hank's Balanced Salt Solution without antibiotics and 0.5 ml can be intranasally inoculated into three-day-old gnotobiotic piglets using a glass Nebulizer (Ted Pella Co., Redding, Calif.). Inoculated piglets can develop clinical signs and microscopic lesions similar to those observed in the spontaneously infected pigs. Lungs, liver, kidney, spleen, heart and brain from these gnotobiotic pigs can be collected eight days after the original inoculation and pooled to prepare another homogenate. This second homogenate can then be inoculated one additional time in gnotobiotic pigs. Again, the same tissues may be collected and homogenized, except that lung tissue can be prepared as a separate homogenate because MSD can be ideally reproduced from the lung homogenate. This lung homogenate represents the second serial passage of the original inoculum (MN 89-35477) in gnotobiotic pigs (Collins et al., 71st Meeting of the Conference of Research Workers in Animal Disease, Abstract No. 2 (1990)). Two filtrates can then be prepared using 0.20 μm filter (Gelman Sciences, Ann Arbor, Mich.) and 0.10 μm filter (Millipore Corp., Bedford, Mass.). These filtrates can be aliquoted and stored at −70° C. All filtrates are free of bacteria and no viruses should be observed on direct electron microscopy using negative stained preparations.

Control Inoculum

Homogenates of lung tissues prepared from two mock-infected gnotobiotic pigs can be used as inoculum in control pigs. This control inoculum can be prepared as 0.20 and 0.10 μm filtrates as described for the MSD inoculum.

Necropsy Procedures and Histopathology

Pigs can be euthanized seven days after the original inoculation as previously described in Collins et al., 71st Meeting of the Conference of Research Workers in Animal Disease, Abstract No. 2 (1990). Tissues can be collected, fixed in neutral buffered formalin, and processed for light microscopic examination as described in Collins et al., Am. J. Vet. Res., 50, 827–35 (1989). Specimens can be collected from turbinates, tonsil, trachea, brain, thymus, lung (apical, cardiac, diaphragmatic lobes), heart, kidney, spleen, liver, stomach, duodenum, jejunum, ileum, ascending and descending colon, blood and mesenteric lymph nodes. These tissues can be processed and then examined using a light microscope to determine whether lymphomononuclear encephalitis, interstitial pneumonia, lymphoplasmacytic rhinitis, lymphomononuclear myocarditis or portal hepatitis is present. Lesions can be consistently observed in spontaneously infected pigs from herds with MSD inoculum (Collins et al., Minnesota Swine Conference for Veterinarians, Abstract, 254–55 (1990)). Fecal contents may also be collected and examined for virus particles as previously described in Ritchie et al., Arch. Gesante. Virusforsche, 23, 292–98 (1968). Blood can be collected for immunologic assays and tissues and cultured for bacteria as described in Example 3.

B. Infectious Agent Isolation

Lung tissue and combined brain-spleen-liver-kidney tissues obtained from an infected piglet in an SIRS-infected herd were homogenized separately. Ten percent homogenates of tissue were used. The individual homogenates were mixed with Minimum Essential Medium (MEM) containing gentamicin at about 100 μg per ml. Both samples were centrifuged at about 4000×g for about 25 minutes. The supernatant was then removed and filtered through a 0.45 micron filter. The tissue and lung homogenates were then combined, and the combined material was used to infect various tissue culture cell lines.

1. In vitro Testing

Two tests were conducted using 75 cm² plastic bottles. In test no. 1, the combined material was inoculated into two bottles of full cell sheet of each of the cell lines listed below. Additionally, to one bottle of each cell line about 2.5 mg of trypsin was added. All other remaining conditions were the same for each bottle of cell line. Serum was not in the culture medium. The inoculum was 1 ml. All bottles were held for seven days at approximately 34° C. The results were recorded at the end of seven days. After freezing and thawing, a sample was taken for a second passage in the same cell line. The remaining material was frozen and stored at about −60° C.

In test no. 2, the combined material was inoculated into one bottle of the same cells as were used in test no. 1. However, the cell sheets were only 20–40 percent confluent at the time of inoculation. The media contained about 10 percent fetal calf serum. Again, the inoculum was 1 ml, and the cultures were incubated at about 34° C. for approximately seven days. The results of both test no. 1 and test no. 2 are summarized below:

| Cell Line Used | Test No. 1 | Test No. 2 |
|---|---|---|
| Bovine Turbinate (BT) | − | − |
| Feline Kidney (CRFK) | − | − |
| Monkey (Vero) Kidney | − | − |
| Monkey (Vero) Lung | − | − |
| Canine Kidney (MDCK) | − | − |
| Porcine (PK2a) Kidney | − | − |
| Mink Lung | − | − |
| Ferret Lung | − | − |
| Bovine Lung | − | − |
| Buffalo Lung | − | − |
| Bovine Kidney (MDBK) | − | − |
| Swine Testicle (ST) | − | − |
| Monkey Kidney (MA-104) | − | + |
| Human Rectal Tumor (HRT-18) | − | NT |
| Human Lung | NT | − |

+ = CPE effect
− = no CPE effect
NT = not tested

There was no cytopathic effect observed in test no. 1 in any of the cell lines evaluated. In test no. 2, however, small clumps of MA-104 cells began to swell and form "weak holes" in the monolayer around the edges of the bottle. Fluid was separated from the bottle, passed into a new bottle of MA-104 cells (again 20–40 percent cell sheet), and then subsequently passed a third time. The cytopathic effect (CPE) became stronger with each passage. The above-described procedures were repeated for the MA-104 cell line employing a full cell sheet. CPE was also observed. Further testing demonstrated that the viral agent will also grow at 37° C. The presence of serum may be helpful for the initial isolation of the viral agent. Subsequent passages of the viral agent in the MA-104 cell line will produce the CPE without the presence of serum. However, more pronounced CPE is observed with the use of serum in the growth medium for the MA-104 cell line.

The viral agent was passaged eight times in the MA-104 cell line with good CPE developing in three days at passage five and greater. The titer obtained is approximately 5=½ logs ($10^{5.5}$). The viral agent will also grow in additional simian cell lines.

2. In vivo Testing

A third passage harvest was used to inoculate two three-day-old gnotobiotic piglets. Both piglets were exposed intranasally, one with 1 ml and the other with 2 ml. The piglets were observed for seven days, and then were euthanized.

Tissue samples were collected for histopathologic examinations and for recovery of the viral agent. The histopathology report confirmed that lung lesions in the infected piglets were identical to lung lesions from piglets known to have SIRS. The tissue samples were processed as before, and then cultured on 20–40 percent and 100 percent monolayers of the MA-104 cell line with bovine, fetal serum. The viral agent was again recovered.

A third passage harvest was also used to inoculate sows in order to verify that the reproductive effects of the disease can be duplicated and confirmed. Two multiparous sows were inoculated intranasally at 93 days of gestation. The sows delivered litters with 50 percent stillbirth piglets (8/13 and 6/14 stillborn/live) on days 112 and 114 of gestation, respectively. Seven of the stillborn piglets were partial mummies and the liveborn piglets were weak and failed to nurse vigorously. The viral agent was recovered from tissues of the stillborn piglets.

The viral agent has been recovered from three herds known to have SIRS. Antibody titers to the ATCC VR-2332 agent have been identified in these same herd Although there are some differences in clinical signs, i.e., cutaneous cyanosis of the ears, tail and udder in European swine, the prevailing opinion is that the North American and European diseases are caused by the same virus, a fastidious, non-hemagglutinating enveloped RNA virus as exemplified by the deposit ATCC VR-2332.

EXAMPLE 1A—FURTHER INFECTIOUS AGENT CHARACTERIZATION

A. Materials and Methods

1. Cells

Crandell feline kidney (CRFK), monkey kidney (MA-104) cells were grown at 37° C. in appropriate cell culture flasks. The CRFK and MA-104 cells were propagated in Eagle's minimum essential media (MEM) (available from Gibco Laboratories, Grand Island, N.Y.) supplemented with 10 percent gamma-irradiated fetal bovine serum (FBS) (available from JRH Biosciences, Lenexa, Kans.), 1 percent penicillin-streptomycin and 2.5 µg/ml of amphotericin B. MA-104 cells were propagated in the same media supplemented with 10 percent FBS and 50 µg/ml of gentamicin. The FBS and cells were confirmed free of bovine virus diarrhea virus (BVDV) using previously described methods of Mayer et al., *Vet. Microbiol.*, 16, 303–314 (1988); Smithies et al., *Proc. Annu. Meet. U.S. Animal Health Assoc.*, 73, 539–550 (1969); and Vickers et al., *J. Vet. Diagn. Invest.*, 2, 300–302 (1990).

2. The Source of the VR-2332 Isolate (SIRS virus)

The source and isolation of the SIRS virus for this Example is set forth below. Virus used in this study was on the 5th to 7th passage in MA-104 cells with titers of $10^5$ to $10^6$ TCID$_{50}$/ml.

Gnotobiotic Pigs

Gnotobiotic piglets obtained by closed hysterotomy were maintained in stainless steel tubs covered by flexible film isolators as previously described by Miniatas O.P. et al., *Can. J. Comp. Med.*, 42, 428–437 (1978). The isolators were maintained at an ambient temperature of 30° C. and pigs were fed recommended amounts of commercial milk substitute three times a day. Fecal swabs were collected prior to experimental inoculation and at necropsy, and were inoculated onto sheep blood agar, tergitol-seven agar and brilliant green agar in aerobic and anaerobic atmospheres. Feces collected at necropsy were also examined for viruses by negative contrast electron microscopy as described by Richie et al., *Arch. Gesante. Virus-forsche*, supra.

Source of Inoculum

A 160-sow farrow-to-finish herd in West Central Minnesota experienced an outbreak of MSD with typical MSD symptoms. A live sow, live neonatal piglets and stillborn fetuses were submitted to the Minnesota Veterinary Diagnostic Laboratory for examination including gross necropsy, histopathology and routine microbial investigation. An inoculum was prepared for experimental use with several tissues from clinically ill neonatal pigs. More specifically, two live and two dead 7- to 10-day-old piglets obtained during the epizootic from the affected herd were necropsied and specimens were collected for diagnostic examinations. The live piglets were euthanized by intravenous injection of euthanasia solution before necropsy. A 10 percent homogenate (MN 89-35477) of brain, lung and tonsil pooled from each pig was prepared using Hank's Balanced Salt Solution (HBSS) containing 100 IU penicillin, 100 µg/ml streptomycin, and 5 µg/ml amphotericin B.

Experimental Transmission

A series of 14 gnotobiotic piglets was challenged at three days of age with pooled tissue homogenates. Each piglet was challenged intranasally by use of a rubber bulb attached to a glass Nebulizer placed in front of the nares of the pig. Initially, two gnotobiotic piglets were inoculated with 0.5 ml each of the unfiltered inoculum (MN 89-35477), monitored for clinical signs of disease, and were euthanized by electrocution seven days post-exposure (PE).

A 10 percent homogenate (designated MNSD-1) of lung tissues pooled from the aforementioned gnotobiotic piglets was blind passaged by exposing each of three gnotobiotic piglets to 0.5 ml of homogenate, one piglet receiving 0.5 ml of unfiltered homogenate, the second receiving 0.45 µm filtrate, and the last one receiving a 0.22 µm filtrate. The piglets were euthanized by eight days PE and tissues were collected for histologic examination, for further passaging in gnotobiotic piglets, and for virus isolation.

A 25 percent suspension of lung (MNSD90x76-L) and a composite of brain, liver and kidney (MNSD90x76-P) of the piglet inoculated with 0.45 µm filtrate of MNSD-1 was prepared using phosphate buffered saline containing 0.5 mg/ml each of kanamycin, streptomycin, and vancomycin. Six gnotobiotic piglets were inoculated with lung homogenate MNSD90x76-L; four piglets received a 0.45 µm filtrate and two were given a 0.1 µm filtrate. Three uninfected, control gnotobiotic piglets were inoculated, one piglet with a 0.45 µm filtrate of uninfected gnotobiotic piglet tissue homogenate in HBSS and two piglets with HBSS alone.

Virus Isolation

Tissue homogenates (MNSD90x76-L and MNSD90x76-P) were centrifuged at 1500xg at 4° C. for 20 minutes. The supernatant was diluted 1:1 with minimum essential medium (MEM) containing 10 µg/ml gentamicin, mixed thoroughly using a Vortex mixer and recentrifuged at 4500xg at 4° C. for 30 minutes. The supernatant was collected and filtered through a 0.45 µm filter. The filtrates from lung and tissue pool homogenates were combined and inoculated onto continuous cell line MA-104. Virus isolation was done in 75 cm$^2$ flasks with 20–40 percent confluent monolayers of MA-104 cells containing 50 ml of MEM (pH 7.5) with 10 percent fetal bovine serum (FBS). Cell cultures were maintained at 34° C. for seven days. If no cytopathic effect (CPE) was observed within seven days, cultures were frozen, thawed and inoculated on MA-104 cells and incubated as above.

Virus Titration

Virus titration was done in 96-well, flat-bottom microtiter plates. Serial 10-fold dilutions of virus were prepared in MEM with 2 percent FBS. After three days, the cell growth medium was drained from the microtiter plates, 200 µl of the virus dilution was placed into each of five wells, and the plates were incubated at 37° C. in an atmosphere of 5 percent CO$_2$. After three days, media in wells with no CPE were replaced with MEM supplemented with 2 percent FBS (pH 7.5) and a final reading was made on the fifth day of incubation. Titers were calculated by the method of Reed et al. in *Am. J. Hyq.*, 27, 493–497 (1938).

3. Other Viruses

Attenuated poliovirus, available from Dr. Roger Koment, Department of Microbiology, University of South Dakota School of Medicine, Vermillion, S. Dak., was propagated on MA-104 cells to a titer of $10^8$ TCID$_{50}$/ml and the Shope strain of pseudorabies virus, available from National Veterinary Services Laboratory, Ames, Iowa; was grown on CRFK cells to a titer of $10^{5-7}$ TCID$_{50}$/ml. These viruses were used as RNA and DNA virus controls in studies to determine the nucleic acid type of the VR2322 isolate of SIRS virus.

4. Preparation of Antisera to VR-2332 Isolate

Passage five of the VR2322 isolate of SIRS virus (titer $10^6$ TCID$_{50}$/ml) was inactivated with 0.25 percent formalin, mixed 1:1 with Freund's incomplete adjuvant, and a rabbit was injected subcutaneously with 2 ml of this suspension at two-week intervals for six weeks. Antisera prepared two weeks after the last injection had a 1:512 neutralizing titer.

5. Virus Neutralization Test (VNT)

MA-104 cells were seeded in flat-bottom, 96-well microtiter plates for the VNT. Serial two-fold dilutions of each serum (100 µl) were prepared in MEM diluent and mixed with an equal volume (100 µl) of isolate VR-2332 containing 100–300 TCID$_{50}$/100 µl. Each mixture was incubated at 37° C. for one hour, and 200 µl of each serum-virus mixture was added to triplicate wells. Microtiter plates were incubated for an additional three days at 37° C., examined by light microscopy for cytopathic effects (CPE), and the endpoint titer expressed as the reciprocal of the highest serum dilution which neutralized CPE.

The following polyclonal antisera, unless indicated otherwise, were prepared as described for the VR-2332 isolate (except viruses were not inactivated) and used in the VNT: the Miller strain of transmissible gastroenteritis; porcine rotavirus serotype 4 (Gottfried); porcine rotavirus serotype 5 (OSU); porcine reovirus serotype 1; porcine enterovirus serotypes 1–8, available from National Veterinary Services Laboratory, Ames, Iowa; monoclonal antibody to porcine parvovirus, available from American Type Culture Collection, Rockville, Md.; encephalomyelocarditis virus, available from Dr. W. Christianson, Department of Clinical and Population Sciences, University of Minnesota, St. Paul, Minn.; pseudorabies virus, available from National Veterinary Services Laboratory, Ames, Iowa; Eastern, Western and Venezuelan equine encephalitis viruses; monoclonal antibody D89 to BVDV described by Mayer et al., *Vet. Microbiol.*, 16, 303–314 (1988); equine arteritis virus, available from National Veterinary Services Laboratory, Ames, Iowa; rubella; and lactic dehydrogenase virus, available from Dr. W. Cafruny, Department of Microbiology, University of South Dakota School of Medicine, Vermillion, S. Dak.

6. Direct Electron Microscopy (DEM)

Cesium chloride gradient fractions were examined by DEM for virus particles as previously described by Benfield et al., *J. Clin. Microbiol.*, 16, 186–190 (1982); Horzinek, "Non-arthropod-borne Togaviruses" (Acad. Press, London, 1981); and Richie et al., *Arch. Gesante. Virus-forsche*, supra, and examined on an electron microscope (Hitachi HU12A, Hitachi, Tokyo, Japan) at a potential of 75 kV.

7. Immune Electron Microscopy (IEM)

Immuno-gold labelling was done using goat anti-rabbit IgG gold colloidal particles (5 nm). Briefly, virus was concentrated at 40,000×g for 30 minutes at 4° C., the pellet was resuspended in 50 µl of distilled water, and 25 µl was placed on a piece of parafilm. A collodion carbon-coated grid was floated on the drop of virus for 15 minutes, blotted dry with filter paper, and placed on a 25 µl drop of rabbit anti-SIRS sera for two minutes. Grids were washed in two changes of 0.1 percent bovine serum albumin (BSA)-Tris buffer for five minutes each and floated for 15 minutes on a drop of gold-labeled antirabbit-IgG. After six washes in BSA-Tris buffer for two minutes each, and two washes in distilled water, the grids were negatively stained and examined as described for DEM.

8. Hemagglutination test (HAT)

The ability of VR-2332 isolate to hemagglutinate sheep, goat, swine, cattle, mouse, rat, rabbit, guinea pig, human type "O", duck, and chicken erythrocytes was determined using standard methods. Two-fold dilutions of the 5th to 7th passage of the VR-2332 isolate of SIRS virus were prepared in phosphate-buffered saline (pH 7.2–7.4) in U-bottom microtiter plates. Equal volumes of a 1 percent suspension of washed erythrocytes from each of the above species were added to each virus dilution, incubated at 4°, 22° or 37° C.; and read after one to two hours when erythrocyte controls (containing no virus) had settled into a button on the bottom of the well.

9. Immunofluorescence (ImF)

Indirect or direct ImF staining of isolate VR-2332 infected and uninfected MA-104 cells was done using the polyclonal or monoclonal antibodies tested by VNT. Swine influenza, available from National Veterinary Services Laboratory, Ames, Iowa (type A, H1N1) and hog cholera virus polyclonal antisera, available, from National Veterinary Services Laboratory, Ames, Iowa, were also used. Scrapings of the cell monolayer were removed at 72 hours PI with a sterile inoculating loop ImF staining as previously described by Benfield et al., *J. Clin. Microbiol.*, supra. Positive control slides were stained either with convalescent antisera from a sow (VNT titer 1:256) or a monoclonal antibody (SDOW 12 or SDOW 17, described herein) to the VR-2332 isolate of SIRS virus.

10. Filtration Studies to Estimate the Size of Isolate VR-2332

Clarified-infected cell culture supernatants were filtered through 0.45 µm (Schleicher and Schnell, Keene, N.H.), 0.20 µm (Schleicher and Schnell, Keene, N.H.), 0.10 µm (Millipore Products Div., Bedford, Mass.) and 0.05 µm (Millipore Products Div., Bedford, Mass.) filters. The infectivity titer before and after filtration was determined using a microtiter assay and a previously described method of Cottral, *Manual of Standardized Methods for Veterinary Microbiology*, pp. 81–82 (Cornell Univ. Press, Ithaca, N.Y., 1978). A 100-fold reduction in infectivity titer was considered significant.

11. Gradient Purification of Isolate VR-2332

The VR-2332 isolate of SIRS virus from clarified culture supernatant was concentrated by centrifugation (Beckman SW 41 Ti rotor) at 200,000×g at 4° C. for 16 hours through a discontinuous sucrose gradient consisting of 2 ml of 20, 30, 40, 50, and 65 percent sucrose (wt/vol) in TNC buffer (10 mM Tris, 100 mM NaCl and 2 mM CaCl, pH 7.8). Culture supernatants were also extracted with 1,1,2-trichlorotrifluoroethane (Sigma Chemical Co., St. Louis, Mo.), concentrated by ultracentrifugation at 100,000×g at 4° C. for one hour, and purified on cesium chloride density gradients (1.20 g/ml) as described for the sucrose gradients. Fractions from either gradient were harvested from the top, the refractive index determined using a refractometer, and selected fractions diluted in Hank's Balanced Salt Solution for virus titration as described above.

12. Chloroform and Fluorocarbon Inactivation

Equal volumes of SIRS virus (VR-2332) and chloroform were mixed periodically for 30 minutes at ambient room temperature and then centrifuged at 500×g at 4° C. for 15 minutes. Similarly equal volumes of 1,1,2-trichlorotrifluoroethane and SIRS virus were mixed on a vortex for five minutes and centrifuged as described for the chloroform treated virus. After centrifugation, the aqueous phase of each treated sample was harvested, diluted, and a microtiter assay used to determine the remaining virus infectivity. A 100-fold reduction in titer of treated compared to untreated virus was considered significant.

13. Effects of Inhibitors of DNA Viruses on Isolate VR-2332

The compounds 5-bromo-2-deoxyuridine (BUDR) and mitomycin C are known inhibitors of the replication of DNA viruses, but do not inhibit RNA viruses with the exception of the Retroviridae (Easternbrook, *Virology,* 19, 509–520 (1962); and Reich et al., *Proc. Natl. Acad. Sci.,* 47, 1212–1217 (1961)). Pseudorabies and poliovirus were used as the known DNA and RNA virus controls in this experiment. Cells (CRFK or MA-104) were seeded in 96-well microtiter plates and duplicate wells were inoculated with 100 μl of ten-fold dilutions of pseudorabies virus, poliovirus or SIRS virus, respectively. After a one-hour absorption period at 37° C., media containing unabsorbed virus was removed and replaced with either MEM (untreated virus controls); MEM supplemented with 40 or 150 μg/ml of BUDR; or MEM containing 2, 10 or 20 μg/ml of mitomycin C. Microtiter plates were incubated at 37° C. for an additional four days, examined by light microscopy for CPE, and the virus titer calculated as described previously by Cottral, supra (1978). A 1000-fold reduction in virus infectivity titer compared to the untreated control was considered significant.

14. Temperature Stability of SIRS Virus

A 2 ml aliquot of virus in MEM was incubated either at 4° C. or in water baths at 37° and 56° C. for at least five days. Aliquots from each tube at the three different temperatures were collected at 15, 30, 60 and 120 minutes and then at 12-hour intervals from 12 to 120 hours. Virus samples were diluted ten-fold in MEM and virus titers calculated as described above.

B. Results

1. Cytopathic Effect of Isolate VR-2332 on MA-104 Cells

Figure 1B:
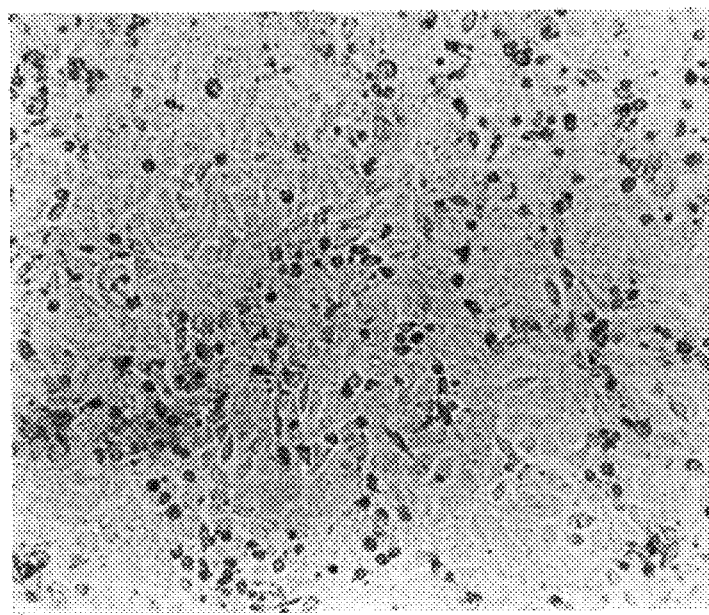
FIG. 1B shows the cytopathic effects observed with a monolayer of cells infected with SIRS virus VR-2332, small granular rounded and degenerating cells observed three days post-innoculation with the 6th passage of the SIRS virus.

The CPE started as small, rounded clumps of cells, which appeared to be raised above the remainder of the uninfected monoayer (FIG. 1B). The number of rounded cells increased and many cells became pyknotic and detached from the monolayer within two to four days PI. By five to six days PI, CPE was evident in 100 percent of the monolayer. Infectivity titers varied from $10^5$ to $10^7$ TCID$_{50}$/1 ml on the 5th and 7th serial passage of virus, respectively. No CPE was observed in uninoculated MA-104 cells (FIG. 1A).

Figure 2A:
FIG. 2A shows the direct immunofluorescence staining of a non-infected monolayer of MA-104 cells.
Figure 2B:
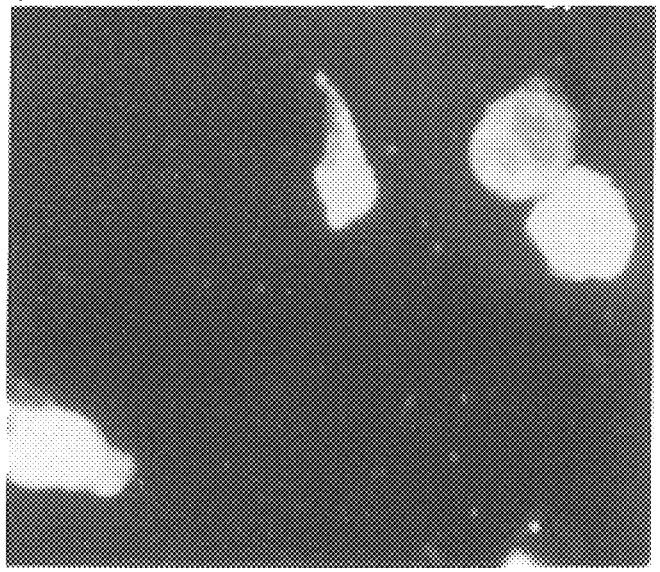
FIG. 2B shows SIRS virus VR-2332 infected MA-104 cells with intense, often granular cytoplasmic fluorescence observed three days post-innoculation.

Fluorescence was not observed in uninoculated MA-104 cells (FIG. 2A). FIG. 2B demonstrates the intense, diffuse fluorescence observed in the cytoplasm of inoculated MA-104 cells stained with either convalescent sow sera, rabbit antisera or monoclonal antibody (prepared to the VR-2332 isolate of SIRS).

2. Effects of Lipid Solvents on the Infectivity of SIRS Virus (isolate VR-2332)

Pretreatment of virus with chloroform eliminated infectivity (titer reduced from $10^5$ to $<10^1$ TCID$_{50}$/1 ml), whereas fluorocarbon treatment had no significant effect.

3. Hemagglutination

Virus did not hemagglutinate erythrocytes from 11 different species irrespective of the temperature of incubation.

4. Estimation of the Size of the SIRS Virus by Filtration

Virus titers were unchanged after filtration through 0.45, 0.20 and 0.10 μm filters. However, infectivity titers were reduced 1000-fold ($10^5$ to $10^2$ TCID$_{50}$/1 ml) after passage through a 0.05 μm (50 nm) filter.

5. Effects of DNA Inhibitors on Replication of the SIRS Virus

Only the infectivity of the DNA virus, pseudorabies, was reduced by either BUDR or mitomycin C. The replication of poliovirus (RNA control) and isolate VR-2332 were not affected, indicating that the genome of the SIRS virus was probably RNA (Tables 1 and 2).

6. Virus Purification

Figure 3:
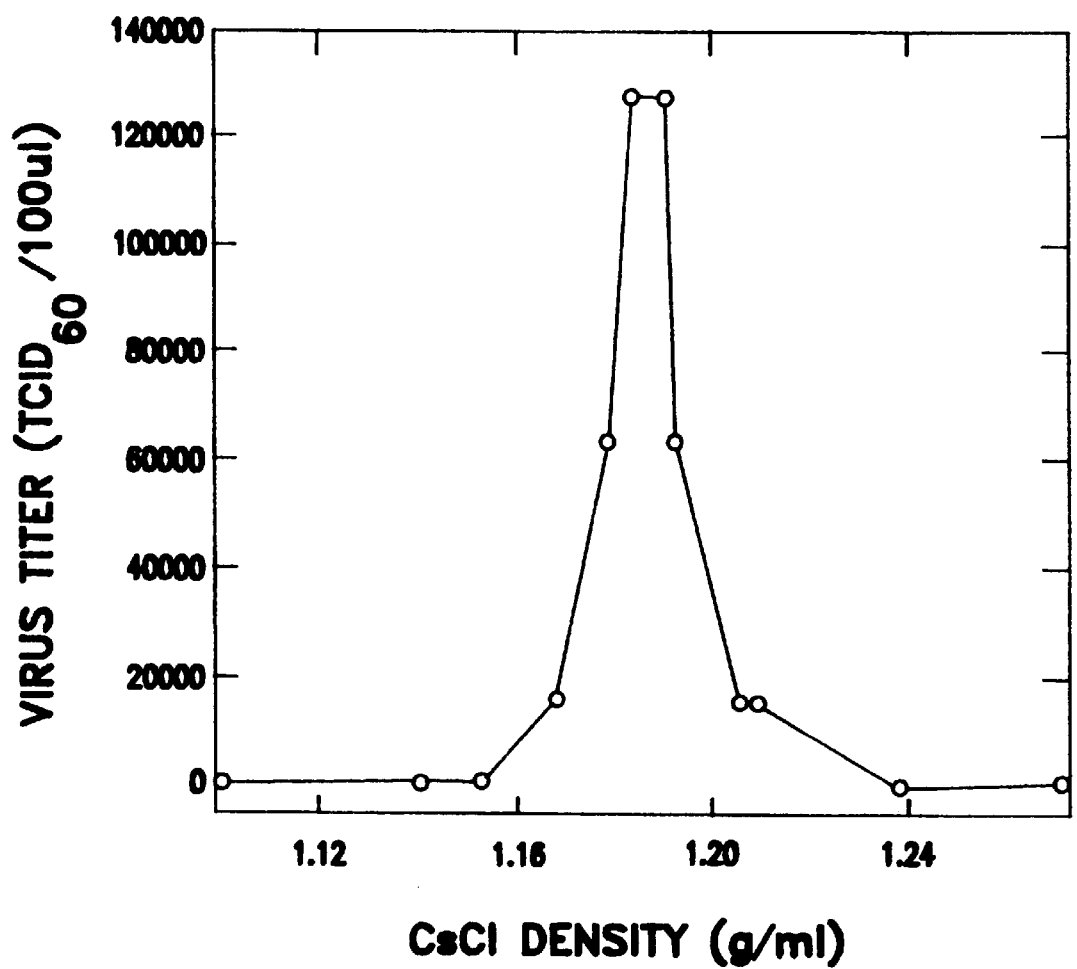
FIG. 3 shows the density gradient profile of SIRS virus purified on CsCl density gradients. Peak virus infectivity occurs at 1.18–1.19 g/ml.

Virus bands were not detected on sucrose gradients, and peak virus titers ($10^4$ TCID$_{50}$/1 ml) were recovered from fractions with buoyant densities of 1.18 to 1.23 g/ml. This peak virus titer was 1000-fold less than the infectivity titer ($10^7$ TCID$_{50}$/ml) of the virus suspension before purification. Cesium chloride gradients yielded a single, faint, opalescent band at a buoyant density of 1.18 to 1.19 g/ml. Peak virus infectivity of $1.3 \times 10^6$ TCID$_{50}$/1 ml, which was 130 times higher than peak infectivity from the sucrose gradient, corresponded to this visible band (FIG. 3).

7. DEM of Purified SIRS Virus Particles

Figure 4A:
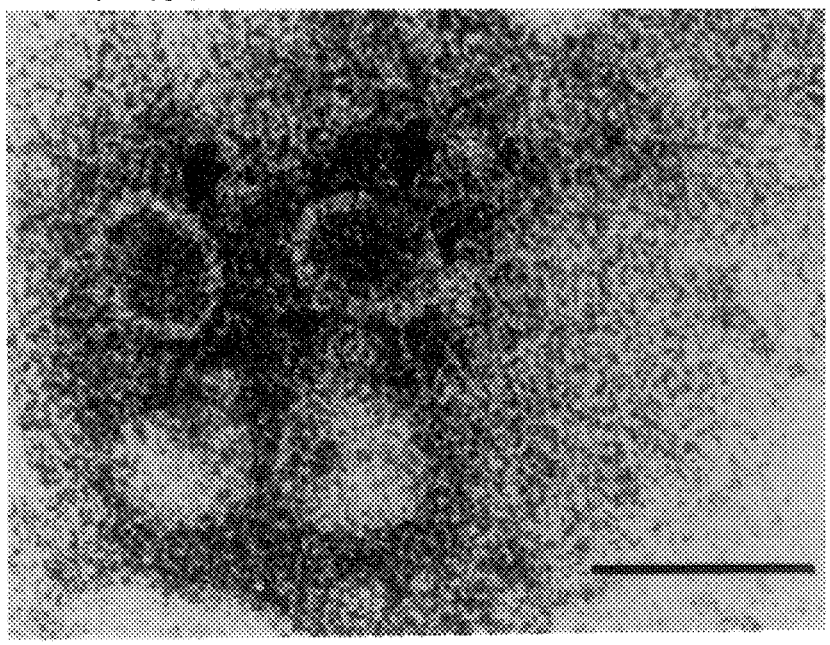
FIG. 4A shows an electron micrograph of virus particles observed in CsCl gradient fractions of density 1.18–1.19 g/ml. These four particles are spherical, 60–65 nm in diameter. Two particles are "empty", showing electron-dense core (arrows), and the other two particles are complete. Bar=100 nm.
Figure 4B:
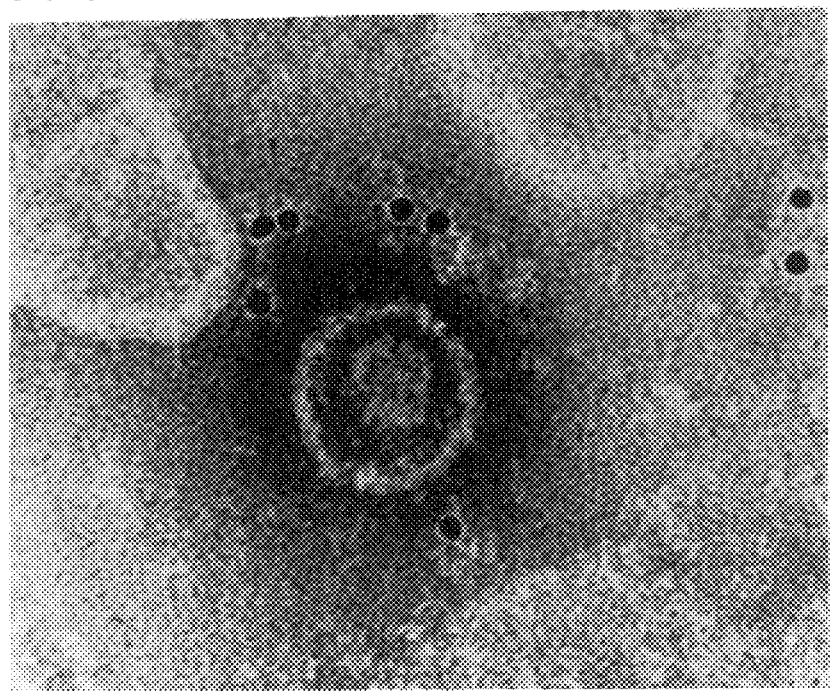
FIG. 4B shows immuno-gold electron microscopy of SIRS virus with hyperimmune rabbit sera and anti-rabbit IgG labeled with gold particles. Note presence of core particle approximately 25–30 nm in diameter within the virion. Bar=50 nm.

Pleomorphic, but predominantly spherical virions were observed by DEM in the CsCl fractions (1.18 to 1.19 g/ml). Virions were 48 to 80 nm (average of 25 particles=62 nm) in diameter and consisted of complete, electron translucent or empty (electron dense center) particles surrounded by a thin membrane or envelope (FIG. 4A). [A 40 to 45 nm diameter isosahedral nucleocapid with short surface projections of about 5 nm in length was observed.] These particles contained cores that were 25 to 35 nm in diameter (FIG. 4B). Virions were immuno-gold labeled if the rabbit hyperimmune antisera and gold-labeled anti-rabbit IgG were used as primary and secondary antibodies (FIG. 4B). Virions were not gold-labeled in the absence of the rabbit hyperimmune antisera to isolate VR-2332.

8. Antigenic Relationship of SIRS Virus to Antisera from Other Viruses

Antisera to known porcine viruses and various togaviruses did not neutralize or react with SIRS virus antigen in infected MA-104 cells. Convalescent sow and hyperimmune rabbit antisera had neutralizing antibody titers of 1:256 and 1:512, respectively.

9. Effects of Temperature on the Infectivity of the SIRS Virus

Figure 5:
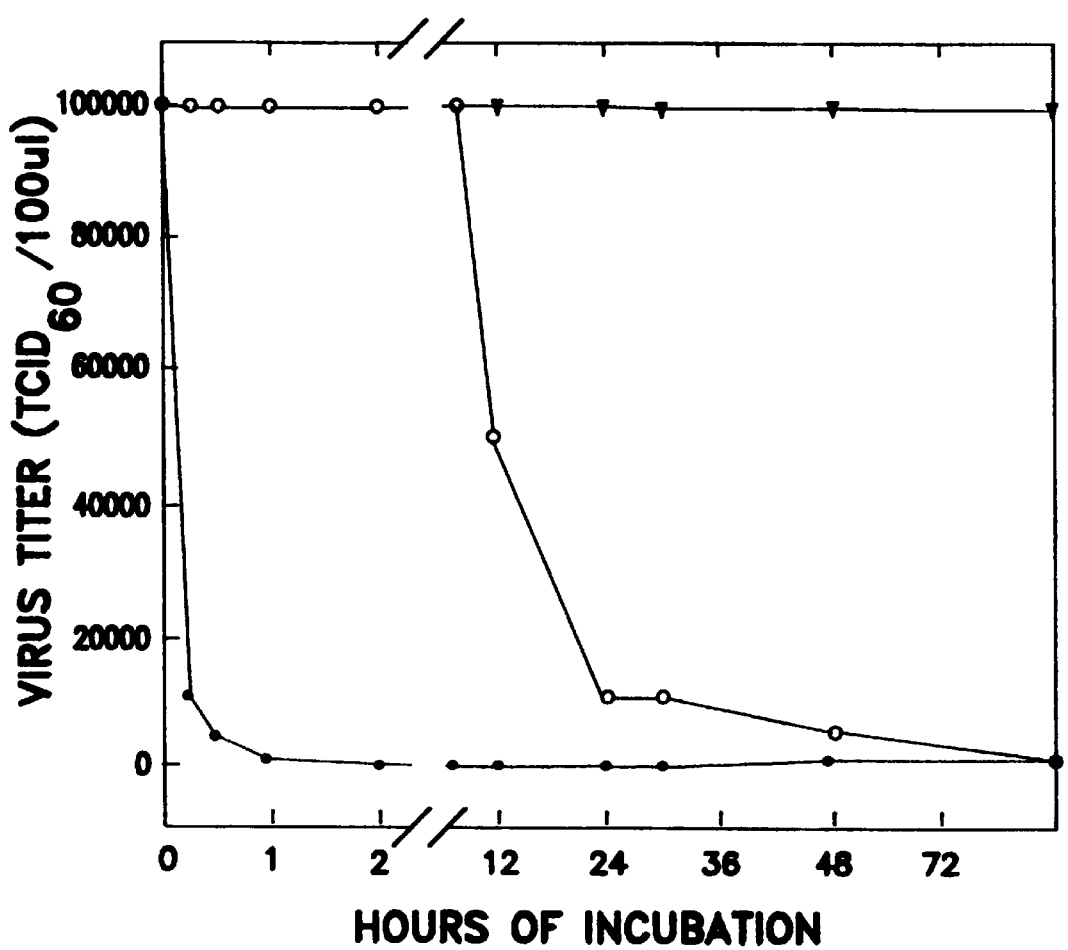
FIG. 5 shows the temperature stability of SIRS virus at 4° C. (open triangles), 37° C. (open circles), and 56° C. (closed circles).

Virus infectivity for MA-104 cells was reduced 50 percent after incubation for 12 hours at 37° C. and completely inactivated after 48 hours of incubation at 37° C. and 45 minutes incubation at 56° C. (FIG. 5). Infectivity was unchanged after one month incubation at 4° C. or four months at −70° C. (data not shown). Lung tissue collected from gnotobiotic pigs infected with SIRS virus and homogenized in Hank's Balanced Salt Solution retains infectivity for pigs for at least 18 months.

Results indicate that isolate VR-2332 is a fastidious, non-hemagglutinating enveloped RNA virus, which can be tentatively classified as a non-arthropod borne togavirus belonging to an unknown genera.

The presence of an RNA genome of the SIRS virus was confirmed by the ability of this virus to continue to replicate in the presence of 5-bromo-2-deoxyuridine and mitomycin C, which are known to inhibit the replication of DNA and one family of RNA viruses (Retroviridae) (Easterbrook, supra (1962); and Reich et al., supra (1961)), but not other RNA viruses. Our provisional classification of the SIRS virus as an RNA virus agrees with the observation that this virus replicates in the cytoplasm of the cell as indicated by the presence of virus antigens detected by ImF.

The VR-2332 isolate of SIRS virus is heat labile, but relatively stable for long periods of time at 4° and −70° C. The thermolability of this virus at 37° C. has practical applications for propagation of the virus, suggesting that growth at temperatures lower than 37° C. will produce higher virus yields. Refrigeration is sufficient for preservation of diagnostic specimens for virus isolation for short periods of time, otherwise the sample can be frozen for several months or longer.

EXAMPLE 2

The purest form of an inoculum with the MSD infectious agent as determined from experiments in Example 1 may be used to transmit the MSD agent to pregnant sows to reproduce the reproductive form of the disease syndrome.
Discussion Recently, transient anorexia and premature farrowing (both prominent clinical signs of MSD in the field) was induced in 2/2 sows inoculated with the same MSD inoculum, which produces respiratory lesions in gnotobiotic pigs. In addition, 15/29 (52 percent) of the pigs were stillborns and the remaining 14 pigs were weak and did not nurse well. No gross or microscopic lesions were observed in the stillborn pigs or the placenta and isolation procedures to detect microbial agents are now in progress. Therefore, the experiment described below tests whether the reproductive form of MSD can be transmitted to sows by intranasal inoculation and whether interference with fetal viability results from replication in maternal tissues but not fetuses.

Experiments in Example 1 provide information on how the inoculum can be treated (filter size, organic solvent extraction and/or protease digestion) to provide the purest form of the MSD agent for an inoculum (i.e., viral agent). Because the MSD agent has both a respiratory form in young pigs and a reproductive form in adult swine, it is necessary to reproduce the latter form of the syndrome to further verify that the infectious agent is the putative cause of MSD.

A 93-day gestational sow is used as the experimental animal because it is possible to experimentally induce abortion in these animals inoculated with the MSD infectious agent. Sows can be purchased from a commercial herd free of ongoing reproductive problems and MSD. Complete epidemiologic records on this herd can be computerized and information on gestation times, litter sizes, and average number of stillbirths can be made available for comparative studies. Groups of three sows each can be intranasally inoculated at 93 days of gestation with either the 0.20 $\mu$m filtrate (positive controls), a pathogenic but modified inoculum as dictated by results from Example 1, a 0.20 $\mu$m filtrate of the control inoculum (negative control), and a control inoculum modified as indicated by results of experiments in Example 1. Each group of sows can be housed in separate isolation rooms and examined daily until gestation is complete. Temperatures and clinical signs (anorexia, respiratory problems such as coughing, sneezing, panting, and increased respiration) can be noted daily. Sampling of sows can be restricted to a pre- and post- farrowing blood sample for serology. The actual date of farrowing can be noted and the number of stillborns, mummified fetuses, live "weak" pigs and live "normal" pigs determined. Fetuses can be examined for gross and microscopic lesions as described in Example 1 and fetal tissues processed for microbiologic assays as described in Example 3. The fetal sera can also be assayed for the presence of gammaglobulins and antibodies to PPV and EMCV (Joo et al., *In Proceedings of the Mystery Swine Disease Committee Meeting*, 62–66 (1990); and Kim et al., *J. Vet. Diagn. Invest.*, 1, 101–4 (1990)). Pigs born live can be observed for one week and morbidity and mortality recorded, after which these pigs can be euthanized and the tissues collected for light microscopic and microbiologic examination as described for the fetuses.

The 0.2 $\mu$m and the modified filtrates of the MSD inoculum are pathogenic for sows and induce anorexia, possibly a mild fever, and premature farrowing with a large number of stillborn and weak pigs in each litter. This illustrates evidence that the inoculum contains the MSD agent. Sows inoculated with the control inoculum farrow near term and have litter sizes within the normal range for the herd of origin as determined from the available epidemiologic database on this herd. No lesions in the stillborn pigs are found and a high rate of mortality among the surviving weak pigs within one week after birth is observed.

EXAMPLE 3

Tissue samples collected from gnotobiotic piglets inoculated with the MSD inoculum and euthanized at various times post-inoculation can be used to isolate and identify the MSD infectious agent to determine the sequential development of lesions, and to ascertain whether the MSD agent is immunosuppressive.
Immunofluorescence Assays on Frozen Tissues and Inoculated Cell Cultures Immunofluorescence assays on frozen tissues and cell scrapings can be done as previously described in Benfield et al., *J. Clin. Microbiol.*, 16, 186–190 (1982) and Benfield et al., *Am. J. Vet. Res.*, 49, 330–36 (1988). The frozen tissues and cell scrapings can be screened for PPV, EMCV (See Example 4 for definition of acronyms) and the MSD agent(s). Conjugates for PPV and EMCV are available at the South Dakota Animal Disease Research and Diagnostic Laboratory. A hyperimmune sera in gnotobiotic pigs can be prepared from the purest form of the MSD inoculum. Two pigs can be inoculated intranasally, and then given a subcutaneous booster of the MSD inoculum in Freund's incomplete adjuvant at two and four weeks after the initial inoculation. Sera can be harvested from this pig two weeks after the last booster. A control sera is also prepared in two gnotobiotic pigs using the control inoculum and the same immunization protocol described for the MSD inoculum. These sera can be used as primary antibody and goat or rabbit anti-porcine immunoglobulin conjugated with fluorescein isothiocyanate as secondary antibody to detect MSD antigens in frozen tissue sections and cell cultures.
Serologic Assays Sera collected from control and inoculated pigs can be assayed for the presence or absence of antibody to PPV and SIV (hemagglutination inhibition), Leptospira (microagglutination), and EMCV (viral neutralization) (see Example 4 for definition of acronyms). Previous results indicated that serology to other common microbial agents were negative (Collins, et al., 71*st Meeting of the Conference of Research Workers in Animal Disease*, Abstract No. 2 (1990)).
Immunologic Assays Tissues and blood can be collected from MSD inoculated and control pigs so that their immunological status can be determined. Porcine leukocytes can be isolated from peripheral blood by single step discontinuous gradient floatation on Histopaque 1077 as taught by Pescovitz et al., *J. Immunol.*, 134, 37–44 (1985). Cells from lymph nodes, spleen and thymus can be spilled into single cells by moderate mincing of the tissues and collection of the resultant cell suspensions (Hurley et al., *Cancer Res.*, 47, 3729–35 (1987)).

Porcine leukocyte phenotypes can be determined using a panel of monoclonal antibodies available through the American Type Culture Collection and Joan Lunney (USDA Beltsville, Md.). These include antibodies for the measurement of total T cells, pCD2 (MSA4; Hammerberg et al., *Vet. Immunol. Immunopathol.*, 11, 107–21 (1986), helper/class II MHC dependent T cells, pCD4 (74-12-4; Lunney et al., *Vet. Immunol. Immunopathol.*, 17, 135–144 (1987), cytotoxicsuppressor/class I MHC dependent T cells, pCD8 (74-2-11; Ibid), macrophages and granulocytes (74-22-15A; Ibid), thymocytes and peripheral B cells, pCD1 (76-7-4; Ibid), and pig MHC class II antigens equivalent to human DRw (MSA3; Hammerberg et al., *Vet. Immunol. Immunopathol.*, 11, 107–21 (1986)) and DQw (TH21A and others (VRMD, Pullman, WA; Davis et al., *Hybridoma Technology in Agriculture and Veterinary Research*, Rowman and Allanheld, 121–50 (1984)). Isotype-specific monoclonal antibodies to porcine immunoglobulins are also available (Paul et al., *J. Vet. Res.*, 50, 471–79 (1989)), and can be used at twice minimum saturating concentration for indirect fluorescent staining of leukocytes from peripheral blood, lymph node, and Peyer's patches (Hurley et al., *Vet. Immunol. Immunopathol.*, 25, 177–93 (1990)). To achieve two-color analysis, cells can also be stained with rPE-labeled avidin after being tagged with biotin-bound (Pierce kit #21333) antibodies. Cells can be analyzed by flow cytometry or a two-color analytical fluorescent microscope (PTI FSCAN system). Co-detection in the 488 nm laser line on the flow cytometer or using the dual analytical fluorescent microscope can easily be attained. Intensity of cellular fluorescence and percentage of positive cells can also be determined.

In vitro functional assays such as lectin mitogenesis with concanavalin A, pokeweed mitogen (PWM), and phytohaemagglutinin (PHA), can be performed as described in Hammerberg et al., *Am. J. Vet. Res.*, 50, 868–74 (1989). Antigen-specific in vitro T cell responses to lysozyme can also be modeled after their technique. B cell proliferative assays can be performed with *E. coli* and *S. typhimurium* LPS or anti-immunoglobulin as reported in Symons et al., *Int. Archs. Allergy Appl. Immun.*, 54, 67–77 (1977). In vitro antibody production, induced with PWM, can be accomplished and quantitated as described in Hammerberg et al., *Am. J. Vet. Res.*, 50, 868–74 (1989). Macrophage production of IL-1 after 48-hour exposure to *E. coli* LPS can be measured in the mouse thymocyte assay (Mizel, *Immunological Rev.*, 63, 51–72 (1982)). IL-2 production by PHA-stimulated lymphocytes can be measured as described by Stott et al., *Vet. Immunol. Immunopathol.*, 13, 31–38 (1986). An isotype-specific anti-lysozyme ELISA can be done utilizing the monoclonal antibodies to porcine immunoglobulin isotypes (Paul et al., *Am. J. Vet. Res.*, 50, 471–79 (1989)).

To assess in vivo antibody production, three piglets inoculated with MSD and three inoculated with control inoculum can be injected with a 2 percent suspension of sheep erythrocytes and a 10 μg/ml solution of bovine serum albumin at separate sites at 5, 7, 10, 14, and 24 days after their original inoculation. Pigs are euthanized at 24 days after the original inoculation, tissues are collected for histopathology as described in Example 1, and blood is collected to assay for antibody. The total antibody level and the specific IgG and IgM responses to each antigen can be measured by antigen-specific radial immunodiffusion or ELISA. Antigen-specific plaque assays can be performed on spleen cells to assess the frequency of B cell clones in the infected and control animals (Kappler, *J. Immunol.*, 112, 1271–85 (1974)).

EXAMPLE 4

Objective

The goal of this experiment is to prepare hyperimmune antisera in a gnotobiotic pig to an isolate of MSD for use as a diagnostic reagent and for further characterization of the antigenic properties of MSD.

Background

Previous studies done in gnotobiotic pigs at South Dakota State University in collaboration with the University of Minnesota indicated that pooled tissue homogenates from field case MN 89-35477 induced lung lesions in gnotobiotic pigs. Pooled tissue homogenates from these pigs have subsequently been used to produce clinical disease and respiratory lesions characteristic of MSD in three-day-old gnotobiotic pigs (Collins et al., *71st Meeting of the Conference of Research Workers in Animal Disease*, Abstract No. 2 (1990) and Collins et al., *Minnesota Swine Conference for Veterinarians*, Abstract, 254–55 (1990)). Lung and tissue homogenates were prepared from this second passage of the original inocula in gnotobiotic pig (90×75) to produce a second inocula. The second inocula can be used as inocula and antigen to produce the hyperimmune sera in this experiment.

Procedure to Accomplish the Objective

Gnotobiotic Pigs

Gnotobiotic pigs can be derived and maintained as previously described in Benfield et al., *Am. J. Vet. Res.*, 49, 330–36 (1988) and Collins et al., *Am. J. Vet. Res.*, 50, 827–835 (1989).

Inoculation of Hyperimmune Sera

Hyperimmune sera can be prepared by initially inoculating one gnotobiotic pig as described above. Pigs can then be given a booster consisting of 1 ml of the second inocula and 1 ml of Freund's Incomplete Adjuvant at 14 and 21 days after the original inoculation (Harlow and Lane, 1988). The pig should then be killed and exsanguinated 14 days or later after the last inoculation. Sera should be harvested and dispensed into appropriate aliquots and frozen at −20° C.

Serology

The hyperimmune sera can be tested for the presence of antibodies to common pathogens of swine as commonly done in most diagnostic laboratories. This sera can be tested for antibodies to Hemophilus, Brucellosis, Leptospira (6 serovars), pseudorabies (PRV), parvovirus (PPV), encephalomyocarditis virus (EMC), and Swine Influenza Virus (SI).

Results

The pig used for preparation of the antisera was pig #4B (experimental number 90×238). This pig was inoculated on Nov. 1, 1990 and observed daily for clinical signs until killed on Nov. 29, 1990. Clinical signs are summarized in Table 1. Unfortunately the continuing degenerate condition of the pig mandated that it be euthanized after only one booster on Nov. 13, 1990. The pig was euthanized 16 days after the initial booster on Nov. 29, 1990.

Serology results were negative for all the above agents except PPV, which had a titer of 16, 384 (See Table 2). A pretitered sera on this pig was not conducted.

Samples of lung, heart, brain, kidney, colon, small intestine, turbinates, spleen, stomach and trachea were collected when the pig was necropsied. These samples were evaluated and it was found that the lungs from this pig had lesions of severe pneumonia typical of that seen with field cases of MSD.

The results of this experiment confirm initial studies that an infectious agent is present in the second inocula because it can induce clinical disease and lesions typical of those observed in natural cases of MSD.

TABLE 1

| Date | Observations of Inoculated Piglet (90 × 238) |
|---|---|
| 10/29 | Surgery |
| 11/1 | Pig inoculated i.n. with 0.5 ml of above inocula using Nebulizer at 5:00 p.m. |
| 11/2 | Not observed. |

TABLE 1-continued

| Date | Observations of Inoculated Piglet (90 × 238) |
|---|---|
| 11/3 | This pig has 2 times as much milk in bowl as the control pigs. I'm not sure how well the pigs are eating or if the agent is the cause of the anorexia. Feces normal. |
| 11/4 | May be a little slow but alert and strong, ½ milk left, feces soft and brown. |
| 11/5 | 9 a.m.: strong, alert, drank most of milk, feces mucoid and brown (2). 4 p.m.: strong, alert, drank most of milk, feces mucoid and brown (2). |
| 11/6 | 9 a.m.: strong, alert, drank ½ of milk, feces brown mucoid (2). 6 p.m.: strong, alert, ½ of milk left, feces loose yellow brown (2). |
| 11/7 | 9 a.m.: strong, alert, drank most of milk, feces light brown mucoid (2). 3 p.m.: strong, alert, drank most of milk, feces light brown mucoid (2). |
| 11/8 | 2 p.m.: Alert, does not drink milk as well as controls, slower than controls, mucoid yellow feces. |
| 11/9 | 8 a.m.: Alert, still does not drink as aggressively as controls, pasty feces. 5 p.m.: same observation as 8 a.m. |
| 11/10 | 6 p.m.: alert, vigorous, rubs snout aggressively against feed pan, feces brown loose, not eating like controls. |
| 11/11 | 6 p.m.: alert, vigorous, rubs snout vigorously against feed pan, feces pasty, not eating as well as controls, still milk in pan, by 6:30 p.m. controls had finished eating. |
| 11/12 | 9 a.m.: alert, but not as aggressive as controls, after 5 minutes the controls have cleaned pans but this pig still has at least ⅔ of milk in bowl. Some snout rubbing. |
| 11/13 | Inoculated with 90 × 75 lg & pool using nebulizer (.5 m) and sp. IFA (1 ml) at 4 p.m. Alert but not as aggressive as controls, still has ½ pan of miik but controls have consumed all their milk. No snout rubbing, feces pasty. |
| 11/15 | 7 p.m.: alert but not as aggressive as controls, still east slow, rough hair coat, but gaining weight like controls. |
| 11/16 to 11/24 | Not much change, alert but steady declining in activity 1 p.m. (11/24): respiration seems to be more, rapid, hair coat is rough, not gaining weight like controls. |
| 11/29 | Euthanized - blood collected for H.I. sera. Usual times collected for histopathology including tonsil. Blood collected for lymphocyte mitogenic assays. No gross lesions noted. Set up turbinate explant cultures. |

TABLE 2

Antibody Tests of Inoculated Piqlet

| | |
|---|---|
| 1. | Swine influenza - negative |
| 2. | Swine Encephalomyocarditis - negative |
| 3. | Swine APP - negative |
| 4. | Swine PRV - negative |
| 5. | Swine PPV - negative |
| 6. | Swine Brucella - negative |
| 7. | Swine Leptospirosa - negative |
| 8. | Swine EPI - negative |

EXAMPLE 4A—MONOCLONAL ANTIBODY PREPARATION

Mouse Immunization

Eight weeks before the date of hybridoma fusion, inoculate BALB/c AnN mice IP with a 1:1 suspension of antigen in Freund's complete adjuvant (CFA). The amount of antigen used is dependent on the immunogenicity and toxicity of the antigen. Use a maximum of 0.3 ml CFA per mouse. Five weeks after the initial immunization, boost mice with antigen in CFA. One week prior to the fusion, immunize mice IP with antigen in saline. Two days before the fusion, inoculate mice IV with antigen in saline.

Myeloma Cells

Maintain mouse myeloma cells (P3/NS-1/1-Ag4-1 (ATCC TIB 18)) on Dulbecco's Modified Eagle Media (DMEM) with 10 percent fetal bovine serum. Approximately $10^7$ to $10^8$ cells are required for fusion with B cells obtained from one typical mouse spleen. Immediately prior to hybridoma fusion, harvest myeloma cells from a log phase culture into a 50 ml centrifuge tube and pellet cells by centrifugation at 200×g for five minutes. Remove the supernatant and wash cells twice with serum free DMEM followed by centrifugation as above. Resuspend the pellet (containing $10^7$ to $10^8$ cells) in 1 ml serum free DMEM.

Isolation of Spleen Lymphocytes

Euthanize the mouse by cervical dislocation and immerse in 70 percent ethanol for several minutes. Remove the spleen by aseptic procedure and transfer it to a sterile petri dish containing 5 ml cold serum free DMEM. Use a scalpel blade to slit the spleen along the long axis and gently scrape along the length of the spleen to release the splenocytes into the media. Use a pipette to transfer the free cells and media to a 15 ml centrifuge tube, leaving the spleen casing behind. Allow the tissue debris in the tube to settle for five minutes and transfer the single cell suspension to a fresh tube. Centrifuge cells for five minutes at 200×g, discard the supernatant and wash the pellet again with cold serum free DMEM. Resuspend cells in 1 ml serum free DMEM and store cells on ice until fusion.

Fusion

Add the spleen cells to the centrifuge tube containing the myeloma cells and centrifuge for five minutes at 500×g. Remove all the supernatant and loosen the cell pellet by tapping on the side of the tube. Keeping all reagents and cells at 37° C., add 1 ml 50 percent polyethylene glycol solution (PEG 4000, Gibco, Grand Island, N.Y.) dropwise to the tube over a one-minute period with gentle mixing. Allow the mixture to stand at 37° C. for one minute. Add 1 ml warm serum free DMEM dropwise over one minute with gentle mixing. Finally, add 20 ml serum-free DMEM dropwise over four minutes, then immediately centrifuge cells at 200×g for five minutes. Discard the supernatant and resuspend cells in 47 ml DMEM containing 20 percent fetal bovine serum, 0.2 units/ml insulin, 0.5 mM sodium pyruvate, 1 mM oxaloacetic acid, 2 mM L-glutamine, nonessential amino acids, and 10 percent NCTC-109 lymphocyte media. Add 1 ml volume of cell suspension to the wells of two 24-well, flat-bottom tissue culture plates. Include a myeloma cell control well and incubate plates at 37° C. and 10 percent $CO_2$ (SDMEM).

Following overnight incubation, remove 0.5 ml of media from each well without disturbing the cell layer. Add 1 ml SDMEM containing $1\times10^{-4}$ M hypoxanthine, $4\times10^{-7}$ M aminopterin, and $1.6\times10^{-5}$ M thymidine (HAT) to each well and continue incubation at 37° C. and 10 percent $CO_2$. Continue to replace 1 ml of used media with 1 ml of fresh DMEM+HAT three times weekly for two to three weeks.

When significant clone growth is apparent, assay the wells for the presence of specific antibody by ELISA, indirect FA, or other appropriate assay systems.

Cloning

Primary wells testing positive for specific antibody should be subcloned immediately to obtain a stable cell line and avoid overgrowth by other clones. Resuspend cells from selected primary wells and perform cell counts using trypan blue stain and a hemocytometer. Make dilutions of the cells to obtain a final concentration of about 2 cells/ml in SDMDM+HT. Use normal spleen cells obtained from non-inoculated mice as a feeder layer by adding 50 μl packed cells per 100 ml media.

Add 250 μl of cell suspension to each well of 96-well plates and incubate at 37° C. and 10 percent $CO_2$. Clones should be visible in two to three weeks and supernatants from wells containing single clones are assayed when significant growth is apparent. Repeat the cloning procedure with wells testing positive for specific antibody. Slowly expand selected clones to tissue culture flasks for further characterization and cryopreservation.

Ascites Production

Prime BALB/c AnN mice with 0.5 ml pristane given IP two weeks before inoculation with hybridoma cells. Harvest hybridoma cells and wash once with Hank's Balanced Salt Solution (HBSS). Resuspend cells in HBSS and inoculate primed mice IP with $10^4$ to $10^6$ viable cells. When ascites production is apparent (usually one to two weeks after inoculation) drain by inserting a 16 G 1½" needle ventrally in the inguinal region. Hold the hub of the needle over a centrifuge tube and drain ascites into the tube. Centrifuge ascites fluid at 200×g, filter through a 0.2 nm filter, and store frozen.

EXAMPLE 4B—SIRS MONOCLONAL ANTIBODIES (SDOW 12 AND SDOW 17)

The SDOW 12 (ATCC No. HB 10996) and SDOW 17 (ATCC No. HB 10997) monoclonal antibodies to the SIRS virus were prepared using the above standard monoclonal antibody production protocol. The antigen used for mouse immunization was passage 6 SIRS virus (VR-2332) grown on MA-104 cells obtained from Boehringer Ingelheim Animal Health (BIAH). For each immunization, mice were inoculated with 0.3 ml of gradient purified virus with a titer of $10^6$ $TCID_{50}/100$ μl.

An indirect fluorescent antibody (IFA) assay was used to detect specific antibody in hybridoma primary wells and clone wells. Acetone fixed virus infected and non-infected cell monolayers in 96-well tissue culture plates were used for the IFA. Cell culture supernatants and ascites fluids from these hybridomas produced bright, granular cytoplasmic fluorescence in SIRS infected cells.

Preliminary characterization of these monoclonal antibodies included immunoglobulin isotyping and radioimmunoprecipitation of SIRS viral proteins. The SDOW 12 and SDOW 17 monoclonal antibodies are both of the $IgG_1$ isotype. They also both bind to a 15 kD viral protein on radioimmunoprecipitation.

EXAMPLE 5

Three pilot studies are described. A gnotobiotic pig study was undertaken to show that field material could be used to infect and cause the respiratory component of the syndrome in germ-free pigs. A second study using conventional weaned pigs was undertaken to determine if the respiratory disease seen in gnotobiotic pigs could be reproduced in conventional pigs. And finally, a pregnant sow study was undertaken to determine if the reproductive failure component of the syndrome could be experimentally reproduced.

Material and Methods

Field Case

See Source of Inoculum in Example 1A.

Gnotobiotic Study

Six hysterectomy-derived gnotobiotic piglets were inoculated intranasally at three days of age with the field inoculum (10 percent homogenates, various tissues). Filtered (0.22 $\mu$m) and unfiltered inoculum were used. Two control piglets were inoculated with media only. Clinical signs were monitored daily and the pigs were euthanized eight days post-inoculation, except one animal which was held for the production of hyperimmune serum. Tissues for virus isolation and histologic examination were collected at necropsy along with sera which was screened for antibodies to leptospira, chlamydia, eperythrozoon, Aujeszky's disease virus, porcine parvovirus, encephalomyocarditis virus, hemagglutinating encephalitis virus, swine influenza virus, bovine respiratory syncytial virus, canine distemper virus, bovine viral diarrhea and hog cholera. The original inoculum and tissues from gnotobiotic piglets were inoculated onto continuous and primary cell lines for three passages. In addition, direct and immunoelectron microscopy was performed.

Conventional Pig Study

Three conventional 28-day-old weaned pigs from a farm with no history of MSD were intranasally inoculated with 10 percent lung homogenates from affected gnotobiotic piglets. A lung homogenate from a negative gnotobiotic pig was used as inoculum for a control. Piglets were monitored daily for clinical signs and were necropsied eight days post-inoculation. Sera/tissues were processed as described above.

Pregnant Sow Study

Eight multiparous sows with known historical due dates from a farm free of MSD were used in this study. Three weeks prior to the expected farrowing date, six sows were intranasally inoculated with affected gnotobiotic lung homogenates and two sows with negative lung homogenates. Clinical signs were monitored daily. The sows were allowed to farrow naturally and when possible the farrowings were attended in order to collect presuckled sera from live born pigs. Sows and live pigs were euthanized shortly after farrowing and tissues were collected for histopathology and virus isolation. Sera or fetal thoracic fluids were also collected.

Results

Field Study

No gross lesions were seen at necropsy. Microscopic examination of nursing piglets revealed necrotizing interstitial pneumonia and lymphomononuclear encephalitis. The fetuses did not have lesions but the sow did have a mild encephalitis. Microbiologic examination did not yield conclusive results.

Gnotobiotic Study

The piglets became anorexic and developed rough hair coats three days post-inoculation. Controls remained-normal. Microscopic lesions were found in the principals inoculated with filtered or non-filtered material. The lesions were similar to field cases and included: necrotizing interstitial pneumonia (6/6 [six out of six piglets]), lymphoplasmacytic rhinitis (4/6 ), lymphomononuclear encephalitis (2/6 ) and myocarditis (1/6 ). No etiologic agent was identified either by pre- and post-inoculation serology or through inoculum/tissue examination.

Conventional Weaned Pig Study Clinically, the principals became dull and anorexic two days post inoculation. The animals appeared chilled even though adequate heat was provided. One pig had an elevated temperature (41.5° C.) six days post-inoculation. Interstitial pneumonia, encephalitis and myocarditis were found in the principals but not the control.

Pregnant Sow Study

Clinically, only two principals showed any significant temperature rises (1.5° C.) day three or five post-inoculation. However, anorexia was noted in 4/6 sows at day four or five post-inoculation. Three sows farrowed up to seven days early and three sows farrowed on time. Over 50 percent of the fetuses from infected sows were born dead while the controls had normal litters. Both stillborns and late-term mummies were found in infected litters. Laboratory findings were not conclusive—no specific agent has been identified and no lesions have been noted in fetuses to date.

Although no causative microorganism has been identified, the findings suggest MSD can be transmitted experimentally to gnotobiotic and conventional pigs (using field tissues from one farm). Both the respiratory and reproductive forms of MSD were reproduced. The agent involved appears infectious, filterable at 0.22 um and is seemingly fastidious.

Discussion

MSD is an important emerging disease not only in the United States but also throughout the world. In order to study the disease in a controlled setting, gnotobiotic pigs were inoculated intranasally at three days of age with tissue homogenates from a farm experiencing the clinical signs of MSD. Microscopic lesions similar to field cases including necrotizing interstitial pneumonia and to a lesser extent lymphoplasmacytic rhinitis, lymphomononuclear encephalitis or myocarditis were seen in principals but not controls. Using lung homogenates from the gnotobiotic pigs, intranasal inoculation of conventional four-week-old weaned pigs produced similar lesions. Multiparous pregnant sows were also inoculated with gnotobiotic lung homogenates three weeks prior to their due dates. Clinically these sows went through a period of anorexia and farrowed up to seven days early. Over 50 percent of the fetuses were either stillborn or in the beginning stages of mummification. The findings indicated the disease associate with the infectious agent can be isolated and transmitted experimentally with field tissues to gnotobiotic pigs and from gnotobiotic pigs to conventional weaned pigs or pregnant sows. This study provides a model for both the respiratory and reproductive forms of the disease which will lead to further investigations of the pathogenesis and diagnosis of MSD.

What is claimed is:

1. A method of producing a swine infertility and respiratory syndrome vaccine containing an attenuated swine infertility and respiratory syndrome virus, the method comprising:

homogenizing tissue from swine affected with swine infertility and respiratory syndrome to form a homogenate which includes swine infertility and respiratory syndrome virus; and attenuating the swine infertility and respiratory syndrome virus in the homogenate by a process comprising passaging the swine infertility and respiratory syndrome virus through simian cells to form attenuated swine infertility and respiratory syndrome virus which is non-zoopathogqnic in swine.

2. The method of claim 1 wherein the simian cells are simian kidney cells.

3. The method of claim 2 wherein the simian kidney cells are MA-104 simian kidney cells.

4. The method of claim 1 wherein the passaging step comprising incubating simian cells inoculated with the swine infertility and respiratory syndrome virus in growth medium including fetal calf serum.

5. The method of claim 1 wherein the passaging step comprising incubating simian cells inoculated with the swine infertility and respiratory syndrome virus until a cytopathic effect is observed.

6. The method of claim 1 wherein the passaging step comprising incubating simian cells inoculated with the swine infertility and respiratory syndrome virus at about 34° C. to 37° C.

7. A method of producing a swine infertility and respiratory syndrome vaccine comprising attenuating swine infertility and respiratory syndrome virus by a process which includes passaging the swine infertility and respiratory syndrome virus through simian cells to from attenuated swine infertility and respiratory syndrome virus which is non-zoopathogenic in swine.

8. The method of claim 7 wherein the passaging step comprises incubating simian cells inoculated with the swine infertility and respiratory syndrome virus at about 34° C. to 37° C.

9. The method of claim 7 wherein the passaging step comprises incubating simian cells inoculated with the swine infertility and respiratory syndrome virus until a cytopathic effect is observed.

10. The method of claim 7 wherein the passaging step comprises incubating simian cells inoculated with the swine infertility and respiratory syndrome virus in growth medium including serum.

11. The method of claim 10 wherein the serum includes fetal calf serum.

12. The method of claim 7 wherein the simian cells are simian kidney cells.

13. The method of claim 12 wherein the simian kidney cells are MA-104 simian kidney cells.

* * * * *

UNITED STATES PATENT AND TRADEMARK OFFICE
CERTIFICATE OF CORRECTION

PATENT NO. : 6,080,570
DATED : June 27, 2000
INVENTOR(S) : Chladek et al.

It is certified that error appears in the above-identified patent and that said Letters Patent is hereby corrected as shown below:

On the title page:

In the section entitled "Related U.S. Application Data", at lines 6-8, delete:

" , which is a continuation-in-part of application No. 07/760,713, Sep. 16, 1991, abandoned"

In claim 4, at line 2, delete "comprising" and insert -- comprises -- therefore.

In claim 5, at line 2, delete "comprising" and insert -- comprises -- therefore.

In claim 6, at line 2, delete "comprising" and insert -- comprises -- therefore.

In claim 6, at lines 3 and 4, after "34°C" and delete ".".

In claim 8, at line 3, after "34°C" and delete ".".

Signed and Sealed this

Eighth Day of May, 2001

*Attest:*

NICHOLAS P. GODICI

*Attesting Officer*       *Acting Director of the United States Patent and Trademark Office*